United States Patent [19]

Katsilometes

[11] Patent Number: 5,340,714
[45] Date of Patent: Aug. 23, 1994

[54] USE OF NONMETALLIC TETRAPYRROLE MOLECULES AND NOVEL SIGNAL SOLUTIONS IN CHEMILUMINESCENT REACTIONS AND ASSAYS

[75] Inventor: George W. Katsilometes, Davis, Calif.

[73] Assignee: Monitor Diagnostics, Inc., Davis, Calif.

[21] Appl. No.: 880,714

[22] Filed: May 8, 1992

[51] Int. Cl.$^5$ .................. C12Q 1/68; G01N 33/72; C09K 11/07
[52] U.S. Cl. .................................. 435/6; 435/7.5; 436/91; 436/97; 436/518; 436/543; 252/700
[58] Field of Search ............... 435/6, 7.5; 436/518, 436/536, 543, 544, 66, 91, 97, 98; 252/700

[56] References Cited

U.S. PATENT DOCUMENTS 4,375,972  3/1983  Forgione ........................ 436/531
4,933,276  6/1990  Baret ............................. 435/7.92

OTHER PUBLICATIONS

Seitz et al "Determination of Trace Amounts of Iron (11) Using Chemiluminescent Analysis", Anal. Chem. 44 #13, (1972) pp. 2143–2149.
Stocker et al "Antioxidant Properties of Conjugated Bilirubin and Biliverdin: Biologically Relevant Scavenging of Hypochlorous Acid", Free Rad. Res. Comm. 6 #1 (1989) pp. 57–66.
Hara et al "Immunoassay Using a Metal–Complex Compound as a Chemiluminescent Catalyst. IV. The Investigation of a Metal Porphine Complex as a Labeling Reagent" Bull. Chem. Soc. Jpn. 57 (1984) pp. 3009–3010.
Weeks, I. et al. (1983) Clin. Chem. 29:1474–1479, "Acridinium Esters as High–Specific–Activity Labels in Immunoassay".
Weeks, I. et al. (1988) Trends in Analytical Chemistry 7:55–58, "Chemiluminescence immunoassays".
Woodhead, J. S. et al. (1988) Complementary Immunoassays, pp. 181–190, W. P. Collins, ed., "Immunochemiluminometric assays".
Gouterman, M. (1978) The Porphyrins, vol. III, David Dolphin, ed., pp. 48–51, 78–87, 115–117, 154–155, "Physical Chemistry, Part A".
Canters, B. W. et al. (1978) The Porphyrins, vol. III, David Dolphin, ed., pp. 577–578, "Physical Chemistry, Part A".
Eastwood, D. et al. (1970) J. Mol. Spectrosc. 35:359–375, "Porphyrins, XVIII. Luminescence of (Co), (Ni), Pd, Pt Complexes".
Simpson, J. S. A. et al. (1979) Nature 279:646–647, "A stable chemiluminescent–labelled antibody for immunological assays".
Fleischer, E. B. et al. (1973) Annals N.Y. Acad. of Sci. 206:32–47, "Relationships Between Porphyrin Structure and Reactivity".

(List continued on next page.)

Primary Examiner—Toni R. Scheiner
Assistant Examiner—Lora M. Green
Attorney, Agent, or Firm—Flehr, Hohbach, Test, Albritton & Herbert

[57] ABSTRACT

Nonmetallic tetrapyrrole molecules are shown to catalyze the production of light by chemiluminescence in the presence of a signal solution at a pH from about 10.0 to about 14.0, having an appropriate oxidant or combination of oxidants and a luminescent reactant. The addition of an electron transport facilitator, a surfactant, a carbohydrate, and a chelating agent to the signal solution increases the output of light. These tetrapyrrole molecules are used alone or attached to haptens or macromolecules and are utilized as labels in the preparation of chemiluminescent, homogeneous or heterogeneous assays. They are also used in conjunction with other chemiluminescent label molecules to produce multiple analyte chemiluminescent assays. A chemiluminescent signal solution which comprises at a pH ranging from about 10.0 to about 14.0 trans, trans-5-(4-Nitrophenyl)-2,4-pentadienal, sodium di-2-ethylhexyl sulfosuccinate, glucose, benzyltrimethylammonium hydroxide, cumene hydroperoxide, trisodium para periodate, potassium superoxide and EDTA with or without a luminescent reactant is also disclosed.

32 Claims, 17 Drawing Sheets

OTHER PUBLICATIONS

Dolphin, D. et al. (1973) *Annals N.Y. Acad. of Sci.* 206:177–200, "The Chemistry of Porphyrin π-Cations".

Tsutsui, M. et al. (1973) *Annals N.Y. Acad. of Sci.* 206:404–408, "Induced Redox Reactions of Metalloporphyrins and Their Implications in Biological Systems".

Kadish, K. M. et al. (1973) *Annals N.Y. Acad. of Sci.* 206:495–503, "Electrochemical Studies of Metalloporphyrins".

Felton, R. H. et al. (1973) *Annals N.Y. Acad. of Sci.* 206:504–515, "Oxidation of Ferric Porphyrins".

Whitten, E. G. et al. (1973) *Annals N.Y. Acad. of Sci.* 206:516–532, "Photochemistry and Redox Activity of Some Metalloporphyrin Complexes".

Wasser, P. K. W. et al. (1973) *Annals N.Y. Acad. of Sci.* 206:533–548, "The Photooxygenation of Metalloporphyrins and Metallochlorins".

Reszka, K. et al. (1984) *Photochemistry and Photobiology* 39:293–299, "Photooxidation of 3,4–Dihydroxyphenylalanine by Hematoporphyrin in Aqueous Solutions: An Electron Spin Resonance Study Using 2,2,6,6–Tetramethyl–4–Piperidone–1–Oxyl (Tempone)".

Gonsalves, A. M. d'A. R. et al. (1991) *Tetrahedron Lett.* 32:1355–1358, "Metal–Assisted Reactions. Part 22. Synthesis of Perhalogenated Porphyrins and Their Use as Oxidation Catalysts".

Ewetz, L. et al. (1976) *Anal. Biochem.* 71:564–570, "Factors Affecting the Specificity of the Luminol Reaction with Hematin Compounds".

Spikes, J. D. (1985) *Primary Photo–Processes in Biology and Medicine*, Benasson, R. V. et al., eds. (Plenum Pub. Corp.), pp. 209–227, "The Historical Development of Ideas on Applications of Photosensitized Reactions in the Health Sciences".

Salokhiddinov, B. M. et al. (1980) *Chem. Phys. Lett.* 76:85–87, "Photosensitized Luminescence of Singlet Oxygen in Solutions at 1588 nm".

Pashchenko, D. I. et al. Translation of: (1982) *Doklady Akademii Nauk SSSR* 265:889–892, "Heterogeneous Catalysis of Chain Transfer to the Monomer in the Presence of an Immobilized Cobalt Porphyrin", Plenum. Pub. Corp. (1983) 0012–5008/82/0008:248–251.

Byteva, I. M. et al. (1987) *Opt Spectrosc. (USSR)* 62:560–561, "Luminescence of singlet oxygen sensitized by an immobilized porphyrin".

Nonell, S. et al. (1991) *Photochem. Photobio.* 53:185–193, "Polymer Bound Pyrrole Compounds–VI. Photophysical Properties of Monomeric Models for Polystyrene–Bound Porphyrins".

Dolphin, D. et al. (1970) *J. Am. Chem. Soc.* 92:743–745, "Isoporphyrins".

Peychal-Heiling, G. et al. (1971) *Anal. Chem.* 43:550–556, "Electrochemical Studies of Tetraphenylporphin, Tetraphenylchlorin, and Tetraphenylbacteriochlorin".

van Steveninck, J. et al. (1988) *Biochem J.* 250:197–201, "The influence of porphyrins on iron–catalysed generation of hydroxyl radicals".

Morehouse, K. M. et al. (1987) *Archives of Biochem.* 257:276–284, "The One–Electron Reduction of Uroporphyrin I by Rat Hepatic Microsome".

Vlasenko, S. B. et al. (1989) *J. Biolum Chemilum* 4:164–176, "An Investigation on the Catalytic Mechanism of Enhanced Chemiluminescence: Immunochemical Applications of this Reaction".

Kricka, L. J. (Nov./Dec. 1990) *Amer. Clin. Lab.*, pp. 30–32, "Bioluminescent and chemiluminescent immunoassays".

Schroeder, H. R. et al. (1978) *Methods in Enzymology* 57:424–445, "Monitoring Specific Protein-Binding Reactions with Chemiluminescence".

Porphyrin Products Catalog, Logan, Utah, p. 5.

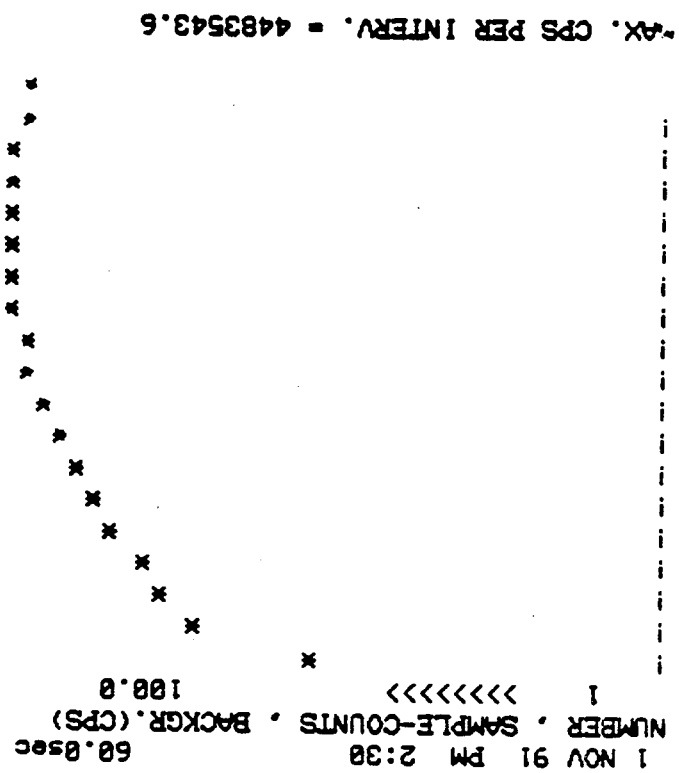
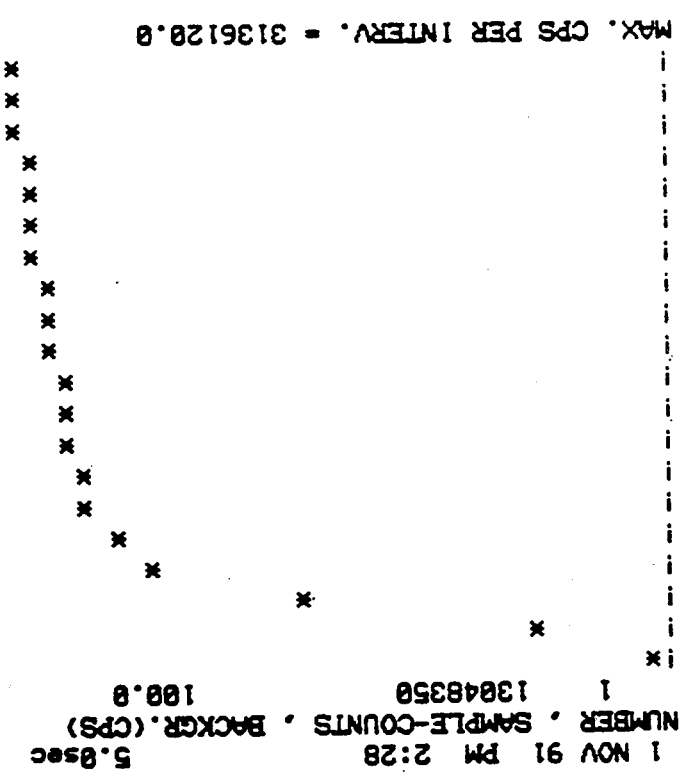
FIG. 14b
FIG. 14a

USE OF NONMETALLIC TETRAPYRROLE MOLECULES AND NOVEL SIGNAL SOLUTIONS IN CHEMILUMINESCENT REACTIONS AND ASSAYS

TECHNICAL FIELD

The present invention relates to the use of nonmetallic tetrapyrrolic molecules as triggers or labels in luminescent reactions and the initiation of light output by novel signal solutions. More particularly, the invention involves the use of a nonmetallic porphyrin, such as deuteroporphyrin IX·2HCl (DPIX) as a chemiluminescent label. The invention further involves a luminescent signal solution comprising a luminescent reactant, at least one oxidant, at least one electron transport facilitator, an ionic detergent, glucose and a chelating agent to produce high yield photon emissions useful in chemical assays, nucleic acid assays and immunoassays. The invention also involves an improvement in existing signal solutions which comprises the addition of potassium superoxide. The invention further reveals the use of a nonmetallic tetrapyrrole label in conjunction with other luminescent labels in simultaneous and sequential assay systems for multiple analytes using multiple labels.

BACKGROUND OF THE INVENTION

Measurement of light energy is becoming a very attractive method for monitoring the presence or concentration of substances in various media. Numerous bioluminescent and chemiluminescent reaction systems have been devised (Schroeder, et al., *Methods in Enzymology*, Vol. LVII: 424–462 (1978); Zeigler, M.M., and T.O. Baldwin, *Current Topics In Bioenergetics*, D. Rao Sanadi ed., (Academic Press):65–113 (1981); DeLuca, M., *Non-Radiometric Assays: Technology and Application in Polypeptide and Steroid Hormone Detection*, (Alan R. Liss, Inc.):47–60 and 61–77 (1988); DeJong, G.J., and P.J.M. Kwakman, *J. of Chromatography*, 492:319–343 (1989); McCapra, F. et al., *J. Biolumin. Chemilumin.*, 4:51–58 (1989); Diamandis, E.P., *Clin. Biochem.*, 23:437–443 (1990); Gillevet, P.M., *Nature*, 348:657–658 (13 Dec., 1990); Kricka, L.J., *Amer. Clin Lab.*, Nov/Dec:30–32 (1990)).

Use of the luminescent molecules lucigenin, acridan dyes and their acridinium derivatives in chemiluminescent reactions and in the development of nonisotopic ligand binding assays has been extensively reported and reviewed (Weeks, I. et al., *Clin. Chem.* 29/8:1474–1479 (1983); Weeks, I. and J.S. Woodhead, *Trends in Anal. Chem.* 7/2:55–58 (1988)). The very short lived emission of photons (<5 sec) to produce the flash-type kinetics in the presence of $H_2O_2$ and NaOH oxidation reagents (pH 13.0) is characteristic of the system.

Luminescence is the production of light by any means, including photoexcitation or a chemical reaction. Chemiluminescence is the emission of light only by means of a chemical reaction. It can be further defined as the emission of light during the reversion to the ground state of electronically excited products of chemical reactions (Woodhead, J.S. et al., *Complementary Immunoassays*, W.P. Collins ed., (John Wiley & Sons Ltd.), 181–191 (1988)). Chemiluminescent reactions can be divided into enzyme-mediated and nonenzymatic reactions. It has been known for some time that the luminescent reactant luminol can be oxidized in neutral to alkaline conditions (pH 7.0–10.2) in the presence of oxidoreductase enzymes (horseradish peroxidase, xanthine oxidase, glucose oxidase), $H_2O_2$, certain inorganic metal ion catalysts or molecules (iron, manganese, copper, zinc), and chelating agents, and that this oxidation leads to the production of an excited intermediate (3-aminophthalic acid) which emits light on decay to its ground state, (Schroeder, H.R. et al., *Anal. Chem.* 48:1933–1937 (1976); Simpson, J.S.A. et al., *Nature* 279:646–647 (14 June, 1979); Baret, A., U.S. Pat. No. 4,933,276)). Other specific molecules and derivatives used to produce luminescence include cyclic diacyl hydrazides other than luminol (e.g., isoluminols), dioxetane derivatives, acridinium derivatives and peroxyoxylates (Messeri, G. et al., *J. Biolum. Chemilum* 4:154–158 (1989); Schaap, A.P. et al., *Tetrahedron Lett.* 28:935–938 (1987); Givens, R.S. et al. *ACS Symposium Series* 383; *Luminescence Applications*, M.C. Goldberg ed., (Amer. Chem. Soc., Wash. D.C.: 127–154 (1989)). Additional molecules which produce light and have been utilized in the ultrasensitive measurement of molecules are polycyclic and reduced nitropolycyclic aromatic hydrocarbons, polycyclic aromatic amines, fluorescamine-labeled catecholamines, and other fluorescent derivatizing agents such as the coumarins, ninhydrins, o-phthalaldehydes, 7-fluoro-4-nitrobenz-2,1,3-oxadiazoles, naphthalene-2,3-dicarboxaldehydes, cyanobenz[f]isoindoles and dansyl chlorides (Simons, S.S., Jr. and D.F. Johnson, *J. Am. Chem. Soc.* 98:7098–7099 (1976); Roth, M., *Anal. Chem.* 43:880–882 (1971); Dunges, W., *ibid*, 49:442–445 (1977); Hill, D.W. et al., *ibid*, 51:1338–1341 (1979); Lindroth, P. and K. Mopper, *ibid*, 51:1667–1674 (1979); Sigvardson, K.W. and J.W. Birks, *ibid*, 55:432–435 (1983); Sigvardson, K.W. et al., *ibid*, 56:1096–1102 (1984); de Montigny, P. et al., *ibid*, 59:1096–1101 (1987); Grayeski, M.L. and J.K. DeVasto, *ibid*, 59:1203–1206 (1987); Rubinstein, M. et al., *Anal. Biochem.* 95:117–121 (1979); Kobayashi, S.-I., et al., *ibid*, 112:99–104 (1981); Watanabe, Y. and K. Imai, *ibid*, 116:471–472 (1981); Tsuchiya, H., *J. Chromatoq.* 231:247–254 (1982); DeJong, C. et al., *ibid*, 241:345–359 (1982); Miyaguchi, K. et al., *ibid*, 303:173–176 (1984); Sigvardson, K.W. and J.W. Birks, *ibid*, 316:507–518 (1984); Benson, J.R. and P.E. Hare, *Proc. Nat. Acad. Sci.* 72:619–622 (1975); Kawasaki, T. et al., *Biomed. Chromatog.* 4:113–118 (1990)).

There are currently three known nonenzymatic systems: the acridinium derivatives (McCapra et al., British Patent No. 1,461,877; Wolf-Rogers J. et al., *J. Immunol. Methods* 133:191–198 (1990)); isoluminols and the metalloporphyrins (Forgione et al., U.S. Pat. No. 4,375,972)). These systems have certain advantages over the enzyme-mediated systems in that they have faster kinetics resulting in peak light output within seconds. The metalloporphyrins are small hapten molecules which decrease stearic hinderance problems in antigen binding. In addition, the only tetrapyrrole molecules previously known to be luminescent are those containing a paramagnetic metal ion with emission yields above $10^{-4}$ (Gouterman, M., *The Porphyrins*, Vol. III, Dolphin, D., ed., (Academic Press): 48–50, 78–87, 115–117, 154–155 (1978); Canters, G.W and J.H. Van Der Waals, *ibid.:* 577–578). It has also been known that metalloporphyrins, hyposporphyrins, pseudonormal metalloporphyrins and metalloporphyrin-like molecules such as metallic chlorins, hemes, cytochromes, chlorophylis, lanthanides and actinides undergo oxidation/reduction reactions which are either primary or secondary to structural perturbations occurring in the metallic center of these molecules and that their reactive ability to catalyze the production of chemiluminescence has been ascribed to the metallo center of these molecules (Eastwood, D. and M. Gouterman, *J. Mol. Spectros.* 35:359-375 (1970); Fleischer, E.B. and M. Krishnamurthy, *Annals N.Y. Academy of Sci.* 206:32-47 (1973); Dolphin, D. et al., *ibid*, 206:177'201; Tsutsui, M. and T.S. Srivastava, *ibid*, 206:404-408; Kadish, K.M. and D.G. Davis, *ibid*, 206:495-504; Felton, R.H. et al., *ibid*, 206:504-516; Whitten, D.G. et al., *ibid*, 206:516-533; Wasser, P.K.W. and J.-H. Fuhrhop, *ibid*, 206:533-549; Forgione et al., U.S. Pat. No. 4,375,972; Reszka, K. and R.C. Sealy, *Photochemistry and Photobiology* 39:293-299 (1984); Gonsalves, A.M.d'A. R. et al., *Tetrahedron Lett.* 32:1355-1358 (1991)). These reactions are altered by iron and other metal ions which may be present in the reactants and these metal ions can interfere with and greatly confound the assay of metalloporphyrin conjugate concentrations (Ewetz, L. and A. Thore, *Anal. Biochem.* 71:564-570 (1976)). Different metals will strongly influence the lifetimes and luminescent properties of the metalloporphyrins.

The following metalloporphyrins will fluoresce: Zn(II), Sn (IV), Mg(II), Pb(II), Al, Cd, Si(IV), Ge(IV), Ba, Sr, Be, Sc(III), Ti(IV), Zr(IV), Hf(IV), Nb(V), Ta(V), Pd(II) and Pt(II). Of these, only Zn(II) could conceivably be incorporated into a nonmetallic porphyrin in aqueous solution at a significant rate, and none would incorporate under strongly basic conditions (personal communication: Jerry C. Bommer, Ph.D.; Porphyrin Products, Logan, UT). Non-fluorescent metalloporphyrins at room temperature are: Fe, Ni, Vo, Ru, Cu, Ag, Co, Rh, and Ir (*Porphyrins and Metalloporphyrins*, Smith, K.M., ed., (Elsevier)).

Metalloporphyrins and nonmetallic porphyrins have both long wavelength electronic transitions and relatively long-lived excited states which make them ideal photosensitizing reagents (Hopf, F.R. and D.G. Whitten, The Porphyrins, Vol. II, Dolphin, D., ed., (Academic Press):162 (1978)). The photoexcited states of the porphyrins are pi, pi, states associated with the porphyrin macrocycle and this photoexcitation can lead to fluorescence and/or phosphorescence (Weiss, C.H. et al., *J. Mol. Spectros.* 16:415-450 (1965); Eastwood, D. and M. Gouterman, *J. Mol. Spectros.* 35:359-375 (1970)). In the case of photoexcitation of porphyrins in general, the sensitizer porphyrin molecule is raised to a short-lived singlet excited state by the absorption of a photon. This singlet state spontaneously converts to an excited triplet state capable of abstracting an electron from adjacent molecules to yield the oxidized high energy intermediate, which on decay to the ground state may emit a photon. The excited triplet state can also transfer excitation energy to ground state molecular oxygen to produce extremely reactive singlet oxygen species, also capable of oxidizing neighboring molecules to their activated intermediates (Spikes, J.D., *Primary Photo-Processes in Biology and Medicine*, Benasson, R.V. et al., eds. (Plenum Pub. Corp.) 209-227 (1985)). It is also known that cobalt, palladium, and, to a lesser extent zinc metalloporphyrins and all monomeric nonmetallic porphyrins are capable of generating high quantum yields of singlet oxygen (0.1-0.2 quanta) in the presence of light and molecular oxygen in solution and when polymer bound (Salokhiddinov, K.I. et al., *Chem Phys Lett* 76:85-87 (1980); Pashchenko, D.I. et al., *Akademiia Nauk SSSR* 265:889-892 (1982); Byteva, I.M. and G.P. Gurinovich, *Opt. Spectrosc (USSR)* 62:560-561 (1987); Nonell, S et al., *Photochem. Photobio.* 53:185-193 (1991)).

Electron transfer and associated chemical reactions of nonmetallic porphyrins in purified aprotic media (dimethylformamide, (DMF)) have been studied using electrochemistry (Wilson, G.S. and B.P. Neri, *Annals N.Y. Academy of Sci.* 206:568-578 (1973)). Polarographic and cyclic voltammetry measurements both demonstrate a two step reversible one-electron reduction of the porphyrin ring followed by a third irreversible two-electron step. Nonmetallic tetrapyrrole porphyrins have also been shown to undergo 2-4 one electron reductions and 2 one electron oxidations. The first reduction product has been shown to be a pi-anion radical (Felton, R.H. and H. Linschitz, *J. Am. Chem. Soc.* 88:1113-1116 (1966)), and the first oxidation a pi-cation radical (Wolberg, A. and J. Manassen, *J. Am. Chem. Soc.* 92:2982-2991 (1970)) by visible and electron spin resonance spectra. The second reduction and oxidation products are the dianion and dication. When the reductions of tetraphenylporphyrin and deuteroporphyrin were studied in more detail, (Dolphin, D. et al., *J. Am. Chem. Soc.* 92:743-745 (1970); Peychal-Heiling, G. and G.S. Wilson, *Anal. Chem.* 43:550-556 (1971)) it was found that the third and fourth reductions were quite complex. Disproportionation occasionally occurred, but the highly nucleophilic materials more often abstracted protons from the solvent.

The redox cycling capability of 5-(4-nitrophenyl)-penta-2,4-dienal (NPPD) to stimulate oxygen uptake and induce superoxide anion and hydrogen peroxide formation in an NADPH-supported enzymatic system has been reported (Docampo, R. et al., *Chem.-Biol. Interactions* (Elsevier Scientific Publishers Ireland Ltd.) 65:123-131 (1988)).

The ability of the enzyme ferredoxin oxidoreductase to generate superoxide, hydrogen peroxide and hydroxyl free radicals from molecular oxygen in the presence of its substrate ferredoxin has been reported (Misra, H.P. and I. Fridovich, *J. Biol. Chem.* 246:6886-6890 (1971); Allen, J.F., *Biochem. and Biophys. Res. Comm.* 66:36-43 (1975); Hosein, B. and G. Palmer, *Biochim. et Biophys. Acta* 723:383-390 (1983); Youngman, R.J. et al., *Oxy Radicals and Their Scavenger Systems*, Vol II, Greenwald, R.A. and G. Cohen, eds., (Elsevier Science Pub. Co., Inc.) 212-217 (1983); Bowyer, J.R. and P. Camilleri, *Biochim. et Biophys. Acta* 808:235-242 (1985); Morehouse, K.M. and R.P. Mason, *J. Biol. Chem.* 263:1204-1211 (1988)). This enzyme produces species which have the possibility of mediating the oxidation of luminol which will in turn lead to the production of measurable photons as in the xanthine oxidase/hypoxanthine system patented by Baret, *supra*. This ferredoxin oxidoreductase system has not, however, been reported on as one which can be used to mediate chemiluminescence.

An augmentation of hydroxyl radical generation in the horseradish peroxidase/$H_2O_2$/NADPH/$Fe^{3+}$-EDTA mixture has been attributed to the addition of uroporphyrin I, haematoporphyrin and haematoporphyrin derivative (Van Steveninck, J. et al., *Biochem. J.* 250:197-201 (1988)). These authors have also demonstrated that rat hepatic microsomal oxidoreductases in the presence of NADPH and uroporphyrin I will generate a porphyrin anion free radical under anaerobic conditions. Aerobic incubations demonstrated the reduction of oxygen to superoxide, but, no oxygen consumption above basal levels could be detected (Morehouse, K.M et al., *Archives of Biochem. and Biophys.* 257:276–284 (1987)).

The use of luminescent reactions at the surface of light conductive materials (e.g., fiber-optic bundle) is the basis of the development of luminescent sensors or probes (Blum, L.J. et al., *Anal. Lett.* 21:717–726 (1988)). This luminescence may be modulated by specific protein binding (antibody) and can be produced in a microenvironment at the surface of the probe. The light output is then measured by photon measuring devices in the formulation of homogeneous (separation free) assays (Messeri, G. et al., *Clin. Chem.* 30:653–657 (1984); Sutherland, R.M. et al., *Complementary Immunoassays*, Collins, W.P., ed., (John Wiley & Sons, Ltd.) :241–261 (1988)).

It has been demonstrated that charged synthetic polymers (poly-N-ethyl-4-vinylpyridinium bromide, PEVP) can completely inhibit the production of light by charged conjugate molecules through electrostatic interactions. This has particularly been studied in the enhanced luminol chemiluminescent reaction catalyzed by the negatively charged peroxidase enzyme. Addition of low-molecular-weight electrolytes will eliminate this inhibition thereby supporting an electrostatic nature of the observed effect (Valsenko, S.B. et al.,*J. Biolum. Chemilum.* 4:164–176 (1989)).

Luminescent capillary electrophoresis gels, gel transfers or blots (Southern, Western, Northern and Dot) are examples of techniques which provide quantitative measurement of proteins and nucleic acid genetic material. These techniques can be used in conjunction with methods which amplify analyte expression, e.g., probes, PCR (polymerase chain reaction) bands, RFLP (restriction fragment length polymorphisms) methods and other methods which amplify gene expression and other analytes (Stevenson, R., *Biotech. Lab.* 8:4–6 (1990)).

A nonmetallic tetrapyrrole as described herein is a tetrapyrrole which has no associated central paramagnetic metal ion.

No ability to chemiluminesce or catalyze or mediate chemiluminescence has ever been attributed to any of the nonmetallic tetrapyrroles including the nonmetallic tetrapyrrole porphyrins or nonmetallic tetrapyrrole porphyrin-like molecules such as the phlorins, porphycenes, secophyrins, texaphyrins and nonmetallic chlorins. For purposes of efficiency as used herein, unless otherwise indicated, the terms "nonmetallic tetrapyrrole" or "nonmetallic tetrapyrrole porphyrin" include nonmetallic tetrapyrrole porphyrin-like molecules.

The use of a novel substance such as a nonmetallic tetrapyrrole to mediate chemiluminescence and/or act as a chemiluminescent label would be extremely beneficial because of the small size of these molecules which would minimize steric hinderance of specific binding protein (such as antibody) to labeled analyte. This would facilitate the ability of the nonmetallic tetrapyrroles to continue to function as chemiluminescent labels following binding to analytes. These nonmetallic labels are not subject to perturbations in activity brought on by the presence of varying types and amounts of heavy metals in samples.

Also it would be beneficial in improving assay sensitivity to increase the output of light obtained from a chemiluminescent reaction by improving existing signal solutions and to have novel signal solutions which provide a greater intensity of light during chemiluminescent reactions. The ability to modulate the kinetics of light output through manipulation of the signal solution formula is particularly beneficial in tailoring assays for a variety of uses (genetic probe, sensor, hormones, etc.).

Nor is there a known chemiluminescent assay for detecting multiple analytes in the same sample. Such an assay would be extremely useful in the area of chemical and medical diagnostics.

SUMMARY OF THE INVENTION

One aspect of the invention is a method for detecting the presence of a nonmetallic tetrapyrrole or its derivative in a sample. The method comprises contacting the sample with a signal solution to produce, by means of chemiluminescence, measurable emitted light and measuring the emitted light with a photometric instrument or device.

A second aspect of the invention is directed to a chemiluminescent system for emitting measurable light useful in a chemical assay, a ligand binding assay, an immunoassay or a nucleotide assay. The system comprises, at a pH ranging from about 10.0 to about 14.0, a nonmetallic tetrapyrrole with a specific energy of activation and oxidation potential, bound to an analyte, or to a binding partner of an analyte or to a ligand of a binding partner to an analyte, a luminescent reactant, an oxidant or a combination of oxidants capable of overcoming the inherent oxidation potential of the tetrapyrrole. In this system the nonmetallic tetrapyrrole acts as a luminescent label (trigger or tag) for the production of chemiluminescence in chemical assays, homogeneous, heterogeneous competitive and sandwich immunoassays, ligand binding assays and nucleotide assays. The light is produced upon exposure of the nonmetallic tetrapyrrole label to a signal solution having the luminescent reactant and oxidant or oxidants. The nonmetallic tetrapyrroles are especially beneficial as the label is more sensitive (i.e., detects smaller quantities of analyte) than most chemiluminescent labels and are able to undergo modification of the kinetics of light production through manipulation of the signal solution formula resulting in stable light producing kinetics for at least 6 seconds. They are also not subject to modulations in light output resulting from the presence of varying amounts of heavy metals in samples.

A third aspect of the invention is a method for using a nonmetallic tetrapyrrole and a luminescent label in a chemiluminescent assay for detecting the presence of a first analyte and a second analyte in a sample. The luminescent label can be various luminescent substances such as lucigenin, a lucigenin derivative, a luciferin derivative, a dioxetane derivative, cyclic diacyl hydrazides such as luminol or isoluminol, a pteridine or an acridinium derivative. The method can be a chemical assay, a nucleotide assay, a ligand binding assay such as an immunoassay (either competitive or sandwich), a sensor assay or it may be a combination of any of these assays. The nonmetallic tetrapyrrole and the luminescent label react to produce light and the amount of light produced determines either directly or indirectly the presence and/or the absence of the analytes in the sample as well as the amounts of the analytes in the sample.

A fourth aspect of the invention is a potassium superoxide ($KO_2$) chemiluminescent signal solution which when reacted with a luminescent label produces chemiluminescence. The signal solution comprises at a pH ranging from about 10.0 to about 14.0 an aqueous solution of potassium superoxide. The preferred labels are the acridinium derivatives, lucigenin, lucigenin derivatives, luciferin, cyclic diacyl hydrazides, luciferin derivatives or a pteridine such as hypoxanthine. With these preferred labels the reaction will produce a signal to noise photon emission ratio of at least 20:1 at 1 ng/ml of label concentration for at least 6 seconds duration.

Another aspect of the invention is a chemiluminescent signal solution which when reacted with a chemiluminescent label that is a luminescent molecule produces chemiluminesence. The signal solution (hereinafter designated "LSS") comprises at a pH from about 10.0 to about 14.0, trans, trans-5-(4-Nitrophenyl)-2,4-pentadienal (NPPD), sodium di-2-ethylhexyl sulfosuccinate (AOT), glucose benzyltrimethyl-ammonium hydroxide (BTAH), cumene hydroperoxide (CH), trisodium para periodate (TNP), potassium superoxide ($KO_2$) and ethylenediaminetetraacetic acid (EDTA). Where the chemiluminescent label is an acridinium derivative, lucigenin, a lucigenin derivative, a cyclic diacyl hydrazide or a pteridine the reaction will produce a signal to noise photon emission ratio of at least 200:1 at 1 ng/ml of label concentration for at least 6 seconds duration.

A further aspect of the invention is a signal solution containing a luminescent reactant which when reacted with a chemiluminescent label or a nonmetallic tetrapyrrole causes chemiluminescence. The signal solution comprises at a pH ranging from about 10.0 to about 14.0 a luminescent reactant and the oxidant $KO_2$ or the combination of oxidants BTAH, CH, TNP and $KO_2$. The chemiluminescent label may be a pteridine, a lucigenin, a lucigenin derivative, an acridinium derivative, a cyclic diacyl hydrazide, a nonmetallic porphyrin, or any number of metallic tetrapyrroles such as a metalloporphyrin, a hyposporphyrin, a pseudonormal metalloporphyrin and a metalloporphyrin-like molecule. The luminescent reactant may be any number of reactants such as luminol, isoluminol, hypoxanthine and isoxanthopterin. With the nonmetallic tetrapyrrole deuteroporphyrin IX·2HCl (DPIX) or any of the other above named chemiluminescent labels and any of the above named luminescent reactants, the reaction produces a signal to noise photon emission ratio of at least 200:1 at 1 ng/ml of chemiluminescent label. Deuteroporphyrin IX·2HCl (DPIX) and the signal solution described in the next paragraph constitute the DPIX system for producing measurable light.

Yet another aspect of the invention is a signal solution containing a luminescent reactant which when reacted with a chemiluminescent label causes a reaction which will produce a signal to noise photon emission ratio of at least 500:1 at 1 ng/ml of chemiluminescent label. The signal solution (hereinafter designated "TSS") comprises at a pH from about 10.0 to about 14.0 trans, trans-5-(4-Nitrophenyl)-2,4-pentadienal, sodium di-2-ethylhexyl sulfosuccinate, glucose, a luminescent reactant, benzyltrimethylammonium hydroxide, cumene hydroperoxide, trisodium para periodate, potassium superoxide and EDTA.

It has also been demonstrated that this signal solution can trigger acridinium derivative and lucigenin chemiluminescence producing a significant increase in light output and a change in light output kinetics from the output obtained with previously known signal solutions.

BRIEF DESCRIPTION OF THE DRAWINGS

FIGS. 9c and 9d show duplicate light output kinetics of the DPIX system and are compared with the kinetics shown in FIGS. 9a and 9b of an acridinium ester system, antithyroid stimulating hormone dimethylacridinium ester (anti TSH-DAE, Ciba Corning). Each readout curve represents 20 measurements over a 2 sec. period of time.

FIGS. 14a and 14b are readouts obtained from a luminometer showing the light output kinetics from separate studies of an acridinium. ester conjugate (anti TSH-dimethylacridinium ester, Ciba Corning, Walpoe, MA) when flashed with TSS signal solution.

FIG. 14a represents the readout curve obtained from 20 light output measurements over a 5 second time period and FIG. 14b represents the readout obtained from 20 separate light output measurements over a 60 second time period.

DETAILED DESCRIPTION OF THE INVENTION

Figure 1:
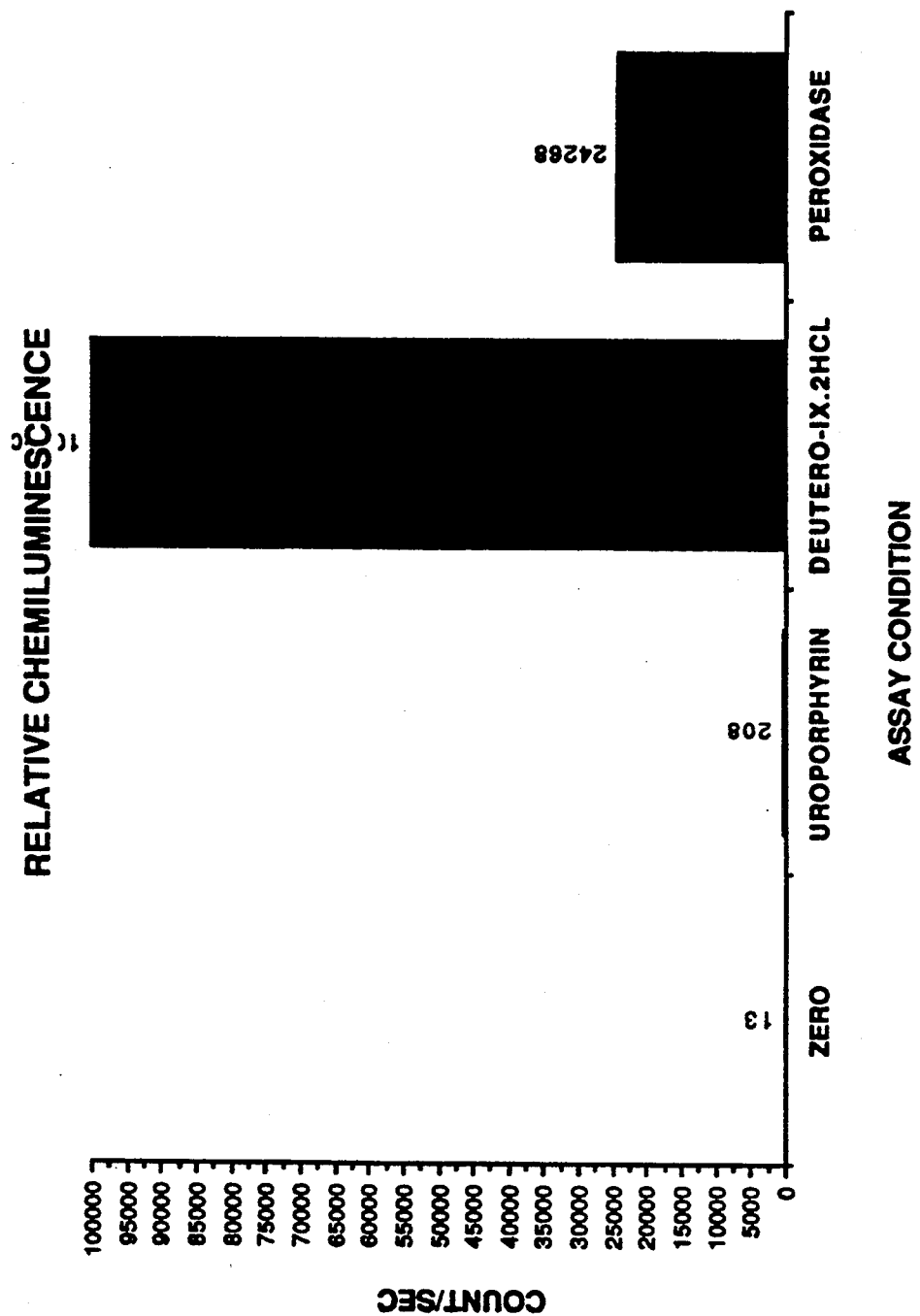
FIG. 1 is a histogram that represents the results of an experiment which compares the relative chemiluminescence in a ferredoxin oxidoreductase/ferredoxin system containing no porphyrin (zero), uroporphyrin I, deuteroporphyrin IX·2HCl (MW 583.51) and horseradish peroxidase.

As defined herein, a signal solution comprises a reagent or group of reagents which when combined with a specific luminescent molecule or a specific luminescence mediating molecule, will cause the production of light. A luminescent label or tag as described herein is a substance bound to an analyte, a binding partner of an analyte, or to a ligand of a binding partner of an analyte either directly (e.g., covalently) or indirectly (e.g., by means of a specific binding substance (protein), a biotin-avidin or biotin-streptavidin bridge) which when combined with a signal solution either produces light or causes light to be produced. A luminescent label may be a luminescent molecule (i.e., the substance which emits light) or it may be a substance which chemically mediates luminescence by initiating an electron exchange causing a luminescent molecule to produce light. Nonmetallic tetrapyrroles act as luminescent labels in this invention. However, unless specifically stated the term "luminescent label" or "chemiluminescent label" is used herein to define a label other than a nonmetallic tetrapyrrole.

As defined herein, a luminescent molecule is a substance, which following electronic excitation by products of a chemical reaction, will emit a photon on decay of orbital electrons to ground state.

As used herein, a luminescent reactant is a free luminescent molecule (i.e., a luminescent molecule that is not bound to an analyte, a binding partner of an analyte or to a ligand of a binding partner of the analyte). Also as used herein the singular term "luminescent molecule" can also include the plural "luminescent molecules". Also, as used herein, the singular term "luminescence mediating molecule" can also include the plural.

The invention is directed to a method for detecting in a sample the presence of a nonmetallic tetrapyrrole having a specific energy of activation and oxidation potential. The method comprises contacting the sample with a signal solution which comprises a luminescent reactant and at least one oxidant capable of lowering the specific energy of activation or oxidation potential of the tetrapyrrole. The tetrapyrrole, the luminescent reactant and the oxidant react to produce emitted light by means of chemiluminescence. A postulated mechanism for the chemiluminescent production of light mediated by nonmetallic tetrapyrroles would begin with the excitement of the tetrapyrrole (porphyrin) by strong oxidants to produce the singlet state discussed by Spikes, supra. This would be followed by the spontaneous conversion to the excited triplet state. It is further hypothesized that this triplet state then abstracts an electron from an appropriate luminescent molecule leading to the formation of the excited intermediate of the luminescent molecule and production of light on intermediate decay to the ground state. In addition, the excited triplet state may excite molecular oxygen forming singlet oxygen which would then oxidize luminescent molecules yielding the excited intermediate which spontaneously decays to ground state while emitting a photon. The light is then measured with a photometric instrument or device such as the Berthold Lumat LB 950 luminometer. This method is more sensitive and more accurate due to lack of interference and self absorption problems encountered with the usual fluorometric methods used to detect nonmetallic tetrapyrroles in solution. For example, this method can be used to detect the concentration of nonmetallic tetrapyrrole photochemotherapeutic agents, such as the nonmetallic chlorin $e_6$ in blood and other fluids.

As with other aspects of this invention which use a nonmetallic tetrapyrrole, because the nonmetallic tetrapyrrole in this invention does not produce light to a substantial degree (i.e., is not the main luminescent molecule) but rather mediates the chemiluminescent light producing reaction, the tetrapyrrole must be contacted with a luminescent reactant as well as an oxidant capable of overcoming the oxidation potential of the tetrapyrrole in order to achieve chemiluminescence. Secondary excitation is the acceptance of energy from an exited molecule. The nucleophilic attack by the oxidant on the tetrapyrrole is sufficient to overcome the inherent oxidation potential of the tetrapyrrole leading to the secondary excitation of the luminescent reactant.

Luminol is the preferred luminescent reactant for use in chemiluminescent reactions of this invention but other luminescent reactants such as isoluminol, pteridines, peroxyoxylates, luciferin, lucigenin, lucigenin derivatives and fluorophors such as fluorescein isothiocyanate and umbelliferones may also be used. A combination of the oxidants benzyltrimethylammonium hydroxide, cumene hydroperoxide, trisodium para periodate and potassium superoxide are preferred for overcoming the oxidation potential of the tetrapyrrole. However, potassium superoxide by itself is also another oxidant capable of overcoming the inheret oxidation potential of the tetrapyrrole. The ferredoxin oxidoreductase/ferredoxin system, described in Example 1, which includes $H_2O_2$ in combination with a nonmetallic tetrapyrrole and luminol will also result in chemiluminescence. Oxidants resulting from the xanthine oxidase/hypoxanthine system of Baret, supra, or the oxidants sodium perborate, cumene hydroperoxide, benzyl trimethyl, ammonium hydroxide, hypochlorite, $H_2O_2$, and oxygen by themselves, however, are not capable of overcoming the inherent oxidation potential of nonmetallic tetrapyrroles (see Table 1, infra.).

The nonmetallic tetrapyrrole porphyrin deuteroporphyrin IX·2HCl (DPIX) is most readily detectable by this method but other nonmetallic porphyrins such as uroporphyrin I dihydrochloride, DPIX 2,4bis glycol, chlorin $e_6$ and mesoporphyrin IX dihydrochloride can also be detected. Nonmetallic linear tetrapyrroles such as bilirubin IX or biliverdin IX hydrochloride are also suitable for detection. This method is highly sensitive and can achieve a limit of $10^{-9}$ detection up to $10^{-18}$ molar of tetrapyrrole (i.e., 1 milligram to 0.001 femtogram/ml of tetrapyrrole) with luminol and the preferred combination of oxidants when the tetrapyrrole is DPIX or up to $10^{-12}$ molar with luminol and potassium superoxide when the tetrapyrrole is DPIX.

The addition of an electron transport facilitator, an anionic surfactant, glucose and a chelating agent to the signal solution also improves the light intensity of the chemiluminescent reaction and subsequently the sensitivity of the reaction. A preferred electron transport facilitator is trans-trans-5-(4-Nitrophenyl)-2,4-pentadienal but other electron transport facilitators such as luteoreticulin and nitroaromatic compounds such as nitrofurans may be used. Sodium di-2-ethylhexyl sulfosuccinate is a preferred ionic surfactant, however, other substances such as lauryl sulfate cetyltrimethylammonium bromide and zwittergent 3-14 may also be suitable. A preferred chelating agent is EDTA but 8-hydroxyquinoline, o-phenanthroline and tetracyclines are also appropriate. The molar detection of DPIX increases from $10^{--}$ to $10^{-20}$ when these additional referred components are added to the signal solution containing the preferred combination of oxidants.

The invention is also directed to a chemiluminescent system for emitting measurable light useful in a chemical assay, in a ligand binding assay such as an immunoassay or in a nucleotide assay. This system comprises at a pH ranging from about 10.0 to about 14.0, a nonmetallic tetrapyrrole having an oxidation potential bound to an analyte or to a binding partner of an analyte or to a ligand of a binding partner to an analyte, a luminescent reactant and an oxidant or a combination of oxidants which is/are capable of lowering the oxidation potential of the tetrapyrrole. Essentially the nonmetallic tetrapyrrole acts as a label (i.e., a tag or tracer) and mediates the production of light in the chemiluminescent reaction. The immunoassay may be homogeneous or heterogeneous and a competitive or sandwich assay. The light is produced by the luminescent reactant by means of chemiluminescence upon exposure of the nonmetallic tetrapyrrole to the proper mix of the appropriate oxidant or oxidants and the luminescent reactant as described above.

This system is particularly useful for detecting an analyte such as a nucleic acid, an antibody, an antigen, a hapten or hapten conjugate, a macromolecule, a protein or a polymer. A binding partner to an analyte in this system may be a nucleotide probe, an antibody, an antigen, a hapten, a hapten conjugate, a macromolecule, a protein or a polymer.

A ligand used herein means a linking or binding molecule and may include an antigen, an antibody, a hapten, a hapten conjugate, a macromolecule, a protein or a polymer other than a protein such as a polyhydrocarbon, a polyglyceride or a polysaccharide.

A hapten conjugate as used herein is a small molecule (i.e., a molecule having a molecular weight of less than 6,000 Daltons) that is attached to another molecule. A particularly suitable conjugate is a steroid molecule-DPIX conjugate. The analyte may be bound to the binding partner or the binding partner may be bound to the ligand by means of a biotinavidin or a biotin-streptavidin bridge. The ligand may also be biotin, avidin or streptavidin and the analyte may also be bound to the nonmetallic tetrapyrrole by means of the biotin-avidin, biotinstreptavidin system. The system provides great sensitivity (up to $10^{-12}$ molar detection of antibody or antigen) when the system comprises DPIX, luminol as the luminescent reactant and potassium superoxide as the oxidant. An even greater sensitivity (up to $10^{-22}$ molar detection of antibody or antigen) is obtained when the system comprises an electron transport facilitator, an ionic surfactant, a chelating agent, glucose, luminescent reactant and a combination of oxidants capable of overcoming the oxidation potential. When the tetrapyrrole is deuteroporphyrin IX·2HCl, the electron transport facilitator is trnas-trans-5-(4-Nitrophenyl)-2,4-pentadienal, the surfactant is sodium di-2-ethylhexyl sulfosuccinate, the luminescent reactant is luminol and the oxidants are benzyltrimethylammonium hydroxide, cumene hydroperoxide, trisodium para periodate and potassium superoxide and the chelating agent is EDTA, the sensitivity is up to $10^{-22}$ molar detection of antibody conjugate. While the chemiluminescent system will be effective at a pH ranging from about 10 to about 14, the preferred pH is from a pH of about 10.5 to 13.0.

The chemiluminescent properties of the nonmetallic tetrapyrrole tag together with the other reagents in the system make the system particularly suitable for the development of ultrasensitive assays for many hapten and macromolecular analytes to which the nonmetallic tetrapyrrole can be directly or indirectly conjugated such as hormones, vitamins, toxins, proteins, infectious and contagious agents, chemicals, drugs, tumor markers, receptors, biotin, avidin, streptavidin and genetic material. The nonmetallic tetrapyrrole can also be directly or indirectly conjugated to a specific binding protein such as an antibody for use in chemiluminometric assay development.

The invention is further directed to a chemiluminescent system for emitting measurable light useful in a chemical assay, an immunoassay, a ligand binding assay or a nucleic acid assay which comprises a luminescent label having a specific oxidation potential, bound to an analyte, or to a binding partner of an analyte or to a ligand to a binding partner to an analyte and a signal solution which comprises, at a pH ranging from about 10.0 to about 14.0, the oxidant, potassium superoxide, or a combination of oxidants comprising benzyltrimethylammonium hydroxide, cumene hydroperoxide, trisodium para periodate and potassium superoxide.

Examples of luminescent molecules for use in this invention are the acridinium derivatives, pteridines, pteridine derivatives, lucigenin, lucigenin derivatives, luciferin, luciferin derivatives, cyclic diacyl hydrazides (luminol or isoluminol), an acridinium derivative such as dimethyl acridinium ester or luciferin and lucigenin derivatives such as those resulting from N-hydroxy succinimide derivatizations are preferred.

A lucigenin derivative as defined herein is a molecule which results from the covalent binding of a reactive group or a group which changes the chemical reactivity and properties of lucigenin leading to the formation of a reactive derivative suitable for conjugation to an analyte or binding partner one wishes to use in assay development. A N-hydroxy succinimide derivatization of lucigenin at one of the two peripheral methyl groups is a preferred lucigenin derivative. A similar derivatization can lead to the formation of a luciferin derivative such as luciferin phosphate.

Again, this chemiluminescent system lends itself to heterogeneous and homogeneous assays including competitive and sandwich immunoassays. The sensitivity of the system is even greater when the signal solution comprises the four oxidants listed above and further comprises an electron transport facilitator, an ionic surfactant, a chelating agent and glucose. When the luminescent label is the acridinium ester, dimethyl acridinium ester, and the electron transport facilitator is trans-trans-5-(4-Nitrophenyl)-2,4-pentadienal, the surfactant is sodium di-2-ethylhexyl sulfosuccinate and the chelating agent is EDTA, the sensitivity is up to the $10^{-22}$ molar detection of conjugate. Again, the analyte may be a nucleic acid, an antigen, an antibody, a hapten, a hapten conjugate, a macromolecule, a protein or a polymer. The homogeneous assay would involve coating the solid phase with the appropriate concentration of luminescent molecule to produce a microenvironment or the use of inhibitors of label luminescence such as polyions. A polycation such as poly(4-vinylpyridinium dichromate) would inhibit, for example, an unbound DPIX labeled compound while a polyanion such as poly(vinylalkyl) would inhibit an unbound positively charged acridinium derivative labeled compound. Unbound in this instance means that if, for example, the compound is an antigen-label conjugate, it is not bound to, for example, an antibody or if the compound is an antibody-label conjugate it is not bound to an antigen, etc. In the case of the homogeneous microenvironment assay using bound luminescence molecule such as luminol, DPIX is a preferred label.

The invention is also directed to a method for using a nonmetallic tetrapyrrole in a chemiluminescent heterogeneous assay for detecting the presence of dual analytes in a sample. Suitable analytes for detection are nucleic acids, antibodies, antigens, haptens, hapten conjugates, macromolecules, polymers or proteins. Again, the method can be a chemical assay, a nucleotide assay or a ligand binding assay such as an immunoassay. The method may also be a combination of any of these assays. The invention involves the conjugation of a nonmetallic tetrapyrrole tag to a first analyte or to a binding partner of that analyte or to a ligand of a binding partner of that analyte and the binding of a different tag or label such as a luminescent molecule or a molecule that mediates chemiluminescence such as an enzyme to a second analyte or to a binding partner of the second analyte or to a ligand of the binding partner of the second analyte. The analytes may be a polynucleotide strand, a chemically active compound such as chlorin $e_6$ or an immunologically active compound such as an antibody, an antigen, a hapten, a hapten conjugate, a macromolecule, a protein or a polymer.

Generally, in the dual sandwich-type immunoassay, a binding partner to one site on the first analyte is attached to a solid phase such as glass, polypropylene, polycarbonate or polystyrene and the, thus, coated solid phase is contacted with the sample and second binding partner for a second site on the analyte. The second binding partner is conjugated to the label (e.g., the nonmetallic tetrapyrrole). The same situation exists for the second analyte only the label and the binding partners are naturally different. The solid phase is washed and the bound conjugates are exposed to the appropriate signal solution or signal solutions. Generally, in a competitive assay, the solid phase is coated with limited concentrations of binding partners specific for each analyte of interest. The solid phase is then contacted with the sample and with a measured amount of first analyte conjugated to the nonmetallic tetrapyrrole and with a measured amount of second analyte conjugated to the other luminescent label. Following contact, the solid phase is washed to remove any unbound conjugate. With both the sandwich-type or competitive-type assay, the washed solid phase may be separately treated first with a signal solution specific for only one of the two labels wherein the label and the solution react to produce emitted light and the amount of analyte related to that specific label may be determined by measuring the amount of light emitted, the solid phase can then be separately contacted with another chemiluminescent signal solution specific for the second label or tag relating to the other analyte whereby that label and signal solution react to produce emitted light. Again, the measurement of the light from the second reaction will determine the amount of second analyte present in the sample.

Since the light produced as a result of the two different labels has different properties (i.e., the wavelength of light given off by means of each label may differ or the actual amount of light produced per second of reaction may differ between the two labels), it is possible to treat the washed phase with a signal solution which will produce light by both conjugates simultaneously, differentiate that light and measure the light to determine the amount of each analyte in the sample. One can differentiate the light given off as a result of the two different labels by utilizing time resolved luminescent analysis such as that used in fluorometry. Lovgren, T. and K. Pettersson, *Luminescence Immunoassay and Molecular Applications,* Van Dyke, K. and R. Van Dyke eds., CRC Ress, Boca Raton, Ann Arbor, Boston, MA, pp. 233-254 (1990).

The differences in emission properties such as wavelengths can also be utilized. Kleinerman, M. et al., *Luminescence of Organic and Inorganic Materials,* Kallmann, H.P. and G.M. Spruch eds., International Conference, New York University Washington Square, sponsored by Air Force Aeronautical Research Laboratory, Army Research Office, Curham Office of Naval Research, N.Y.U., pp. 197-225 (1961).

A preferred luminescent label for the dual analyte assay is an acridinium derivative such as dimethyl acridinium ester or a lucigenin derivative but several other luminescent labels previously discussed are also suitable. A preferred nonmetallic tetrapyrrole is DPIX. The preferred signal solution for producing emitted light by means of more than one label (e.g., by means of the labels of both analyte conjugates) simultaneously comprises at a pH from about 10.0 to about 14.0, trans,-trans-5-(4-Nitrophenyl)-2,4-pentadienal, sodium di-2-ethylhexyl sulfosuccinate, the luminescent reactant luminol, glucose, benzyltrimethylammonium hydroxide, cumene hydroperoxide, trisodium para periodate, potassium superoxide and EDTA. The same signal solution without the luminescent reactant can be used in this dual assay to flash a luminescent molecule bound to an analyte. If one of the analyte conjugates is an enzyme labeled analyte conjugate the substrate for that enzyme will have to be included in the signal solution. A signal solution which comprises at a pH ranging from about 10.0 to about 14.0, potassium superoxide or the combination of oxidants, benzyltrimethylammonium hydroxide, cumene hydroperoxide, trisodium para periodate and potassium superoxide is also suitable in this assay to flash the luminescent molecule label.

In addition, the invention is directed to a chemiluminescent homogeneous assay for detecting dual analytes in a sample. In a competitive-type assay, the solid phase is coated with a binding partner specific for each different analyte. The solid phase may additionally be coated with a luminescent reactant in cases where a tetrapyrrole is used as one of the labels. The thus coated solid phase is then contacted with the sample, with a known amount of one of the analytes conjugated to a nonmetallic tetrapyrrole label, with a known amount of the other analyte conjugated to a different luminescent label and with a polyion such as poly-N-ethyl-4-vinylpyridinium bromide, poly-4-vinylpyrimidinium dichromate, polyvinylchloride, poly(vinylalcohol), poly(vinylbenzyl chloride) capable of inhibiting unbound different luminescent label conjugate such as anti-TSH dimethyl acridinium ester (e.g., poly(vinylalcohol), polyanion) by preventing the overcoming of the oxidation potential of the luminescent label of the unbound conjugate (Vlasenko, S.B. et al, J. Biolum. Chemilum. 4:164–176 (1989)). Following contact, the solid phase is then treated with a signal solution capable of either producing emitted light by means of both conjugates simultaneously or separately contacting the solid phase with a signal solution specific for one label and measuring the emitted light and then separately contacting the solid phase with a signal solution specific for emitting light by means of the label of the other conjugate.

The invention also includes an improved signal solution wherein the improvement is the addition of potassium superoxide. The original signal solution must be one that has at an alkaline pH and at least one oxidant capable of oxidizing a luminescent label to produce measurable light. Examples of suitable signal solutions appropriate for the addition of potassium superoxide include those of Baret, supra., and Forgione, supra. and $H_2O_2$ followed by NaOH. The preferred concentration of $KO_2$ is 5 mM but a concentration from about 0.5 mM to about 50 mM is also applicable.

The invention is additionally directed to a chemiluminescent signal solution which comprises at a pH ranging from about 10.0 to about 14.0 an aqueous solution of about 0.5 mM to about 50 mM potassium superoxide, preferrably 5 mM in a buffered solution. The preferred buffer is trizma base but other solutions such as sodium tetraborate and boric acid also work well. The preferred luminescent molecules for use as labels in conjunction with this signal solution are the acridinium and lucigenin derivatives (see, Table 1, infra). However, isoluminol alone and deuteroporphyrin IX·2HCl in conjunction with the luminescent reactant luminol when used with the $KO_2$ signal solution are also suitable labels. When this solution is reacted with a luminescent molecule such as dimethyl acridinium ester or lucigenin or a luminescent label conjugate such as estradiol 17β-DPIX or anti TSH-dimethyl acridinium ester, a signal to noise photon emission ratio of at least 20:1 at 1 ng/ml of label concentration is produced for at least 6 seconds (see FIG. 14).

The invention is further directed to a chemiluminescent signal solution which comprises at a pH from about 10.0 to about 14.0, trans, trans-5-(4-Nitrophenyl)-2,4-pentadienal, sodium di-2-ethylhexyl sulfosuccinate, glucose, benzyltrimethylammonium hydroxide, cumene hydroperoxide, trisodium para periodate, potassium superoxide and EDTA (LSS). This novel signal solution can trigger acridinium ester derivative chemiluminescence producing a significant increase in light output and a change in light output kinetics from the output obtained with previously known signal solutions. When this solution is reacted with a luminescent label or a luminescent label conjugate such as lucigenin-antibody or anti TSH-dimethyl acridinium ester, a signal to noise photon emission ratio of at least 500:1 at 1 ng/ml of label concentration is produced for at least 6 seconds.

In addition, the invention is directed to a signal solution which comprises, at a pH ranging from about 10.0 to about 14.0, a luminescent reactant, trans, trans-5-(4-Nitrophenyl)-2,4-pentadienal, sodium di-2-ethylhexyl sulfosuccinate, glucose, benzyltrimethylammonium hydroxide, cumene hydroperoxide, trisodium para periodate, potassium superoxide and EDTA. It is preferred in all aspects of the invention where this signal solution is used that it be prepared according to the procedure described in Example 3 with respect to components, sequence of component addition and component concentration. However, other concentrations which are also suitable are:

$KO_2$: 0.1–2.0 mg/ml of buffer solution
NPPD: 0.5–2.5 μl of 10 mM NPPD in DMSO solution/ml of buffer
BTAH: 1–8 μl of a 40 wt. % solution/ml of buffer
Cumene Hydroperoxide: 0.1–0.35 μl of an 80% solution/ml buffer
Glucose: 2–20 mg/ml of buffer
Luminol: 0.01–0.05 mg/ml; (14 μl of 0.004–0.025 M luminol in $dH_2O$; pH 10.2 ml of buffer)
EDTA: 0.5–2.0 μl of 5 mM EDTA/ml of buffer
Tri Na para periodate (TNP): 2–10 μl of a 20 mM solution in 0.2 M acetic acid/ml of buffer
Surfactant (AOT etc.): 10–80 μl of a 5–25 mM solution in $dH_2O$/ml of buffer Chemiluminescence mediating, luminescent labels that may be used to obtain chemiluminescence with this solution are any number of metallic tetrapyrroles such as metalloporphyrins, hyposporphyrins, pseudonormal metalloporphyrins and metalloporphyrinlike molecules (vitamin $B_2$), but the preferred labels in this instance are the nonmetallic tetrapyrroles such as deuteroporphyrin IX·2HCl. Luminescent molecules may also be used as luminescent labels. Such suitable labels include the acridinium derivatives and the lucigenin derivatives. This signal solution was used to flash various free molecules and luminescent molecule containing substances such as hemoglobin, vitamin $B_2$, horse serum albumin, bovine serum albumin and coenzyme A. These molecules may also be derivatized and used as luminescent labels. The luminescent reactant may be any of the luminescent reactants previously discussed but luminol is preferred. When this solution is reacted with a luminescent label that mediates chemiluminescence such as lucigenin or DPIX, the luminescent reactant produces a signal to noise photon emission ratio of at least 290:1 at 1 ng/ml of luminescent label.

EXAMPLE 1

Assay of Metallic and Non-Metallic Porphyrin in a Ferredoxin Oxidoreductase/Ferredoxin System The assay was as follows: 100 μl of a signal solution containing 0.88 ml of a luminol solution (88.6 mg/50 ml $H_2O$), 0.1 ml of Na-perborate solution (60 mg sodium perborate/20 ml borate buffer, pH 10.3), and 0.5 ml of an FeEDTA solution (232 mg NaEDTA and 8.4 mg $FeC_3·gH_2O$ in 50 ml $dH_2O$) in 100 ml of a borate buffer (0.2 mol/L; ph 10.3) were added to 200 μl of 0.5 mM NADPH, 200 μl ferredoxin (1 mM in borate buffer, pH 10.3), and 200 μl ferredoxin oxidoreductase (50 pM, 0.02 units/ml). The light output resulting from this assay was measured on a Berthold Lumat LB 9501 luminometer.

FIG. 1 shows that the ferredoxin oxidoreductase/ferredoxin system by itself in the presence of oxidants and luminol led to the production of a very minimal amount of light (zero, Bar 1, i.e., the far left bar). When 50 μl of 50 μM uroporphyrin I dihydrochloride (uroporphyrin) (Porphyrin Products, Logan, UT) was included in the same ferredoxin/oxidoreductase/ferredoxin/H$_2$O$_2$/NADPH reaction mixture, a slightly increased output of light was observed (Bar 2). However, when 50 μl of 50 μM nonmetallic deuteroporphyrin IX·2HCl (DPIX) (Porphyrin Products, Logan, UT) was added to the same ferredoxin oxidoreductase/ferredoxin reaction mixture, a surprising light output which exceeded the capacity of the Berthold Lumat LB 9501 luminometer was produced (Bar 3). The addition of 50 μl of horseradish peroxidase (50 μM, 0.02 units/ml) to the same reaction mixture resulted in a light output equivalent to only about one third of the output observed with DPIX (Bar 4).

EXAMPLE 2

Figure 2:
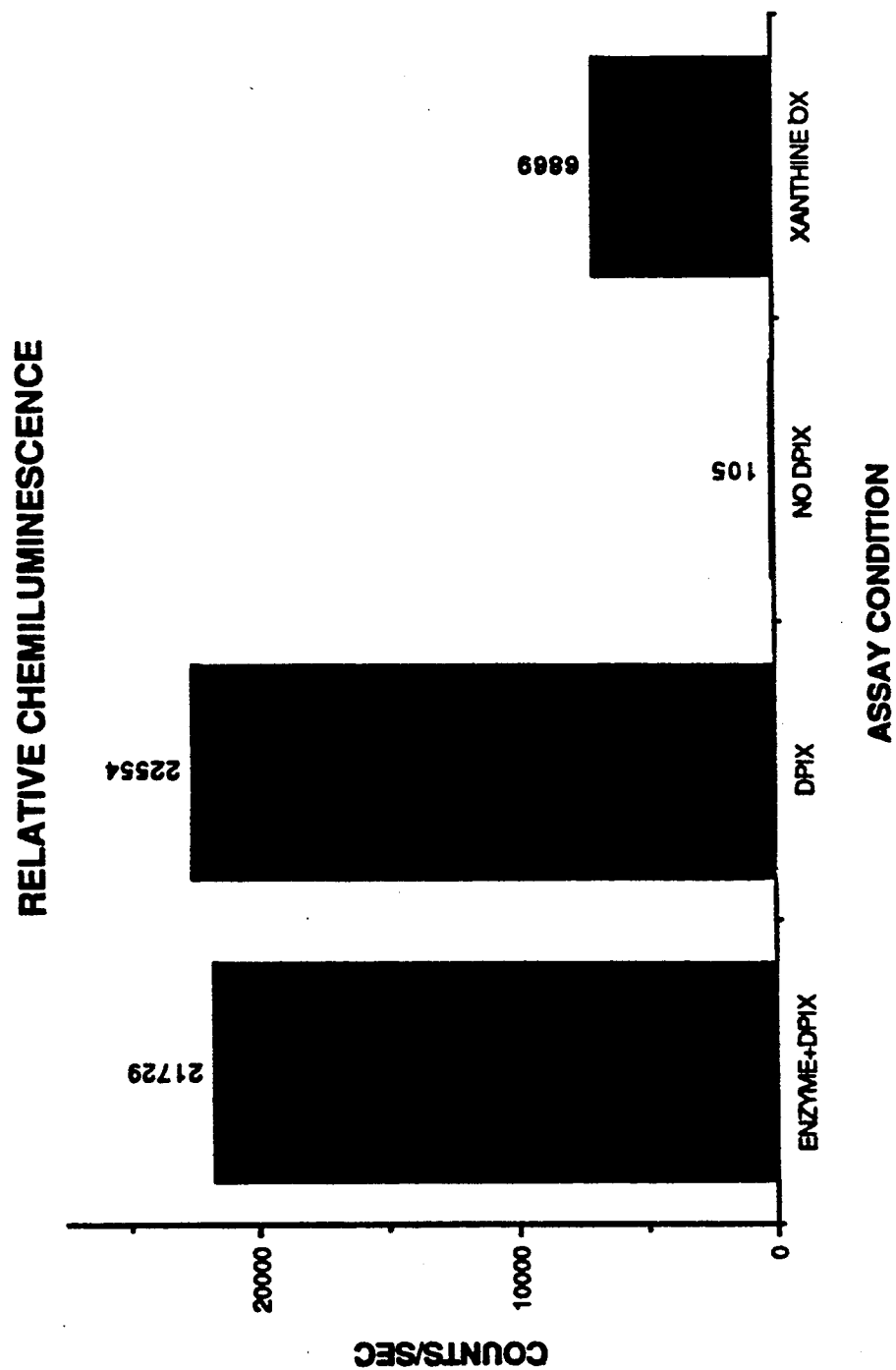
FIG. 2 is a histogram that represents the results of an experiment which compares the relative chemiluminescence between the ferredoxin oxidoreductase/ferredoxin system with DPIX (Bar 1) and without DPIX (Bar 3), and the xanthine oxidase/hypoxanthine system without DPIX (Bar 4), and DPIX without enzyme/substrate (Bar 2).

Assay Comparing Variables of DPIX in the Ferredoxin Oxidoreductase/Ferredoxin and Xanthine Oxidase/Hypoxanthine Systems As shown in FIG. 2 this example compared the relative chemiluminescence in a ferredoxin oxidoreductase/ferredoxin enzyme/substrate system with (Bar 1) and without DPIX (Bar 3) to DPIX without ferredoxin oxidoreductase and ferredoxin (Bar 2) and to the xanthine oxidase/hypoxanthine system without DPIX (Bar 4). Unless otherwise stated, conditions for this experiment were the same as for Example 1. For the xanthine oxidase/hypoxanthine system comparison, concentrations of xanthine oxidase and hypoxanthane equimolar to the concentrations of ferredoxin oxidoreductase and ferredoxin disclosed above were used. Otherwise signal solutions identical to the signal solution of Example 1 were utilized. The light output was also measured on a Berthold luminometer Bar 1 shows the addition of 10 μl of 0.5 μM DPIX to the ferredoxin/ferredoxin/oxidoreductase system; Bar 2 shows the addition of signal solution to 10 μl of 0.5 μM DPIX minus ferredoxin/ferredoxin/oxidoreductase; Bar 3 shows the ferredoxin/ferredoxin/oxidoreductase system light production, and Bar 4 is the same signal solution using hypoxanthine and xanthine oxidase.

EXAMPLE 3

Assay Comparing DPIX and DPIX Conjugates

This example compared the signal obtained with 100 picomolar concentrations of native DPIX in dH$_2$O, anti-mouse DPIX conjugate prepared according to Example 7, infra, and estradiol-17β-BSA-DPIX conjugate concentrations prepared after the protocol in Example 7. The conditions for this assay were the addition of 35 μl of 1 μg/ml of label (i.e., DPIX or DPIX conjugate) solution to a tube followed by flashing with 265 μl of the signal solution formulated below (FIG. 3).

The TSS signal solution was formulated by adding 75 μl of 10 mM trans,trans-5-(4-Nitrophenyl)-2,4-pentadienal (NPPD, Aldrich) in DMSO, 1400 μl of 1% AOT, and 700 μl of a 5-amino-2,3-dihydro-l,4-phthalazinedione (luminol; Sigma) solution (consisting of 880 μl of 10 mM luminol in H$_2$O added to 100 ml of 0.1 M Trizma base in dH$_2$O) to 50 ml of 0.1 M Trizma base. Trizma base is preferred but other bases such as sodium tetraborate and a boric acid solution are also suitable. The signal solution was then brought to pH 12.3 with 10 N NaOH. Immediately following the adjustment of pH, 170 mg of glucose was added with mixing. A series of oxidants and a chelating agent were then added with mixing, beginning with 100 μl of benzyltrimethylammonium hydroxide (Aldrich), 9 μl of cumene hydroperoxide (80% Sigma), 200 μl of 20 mM trisodium para periodate (G. Frederick Smith Chemical Co., Columbus, OH) in 0.2 M acetic acid, 17.5 ml of 20 mM potassium superoxide (KO$_2$, Aldrich) in dH$_2$O and 50 μl of 5 mM ethylenediaminetetraacetic acid (EDTA, Sigma) in dH$_2$O. The signal solution was stored at 4° C. This signal solution was and can be utilized following a 12 hour period which allows the background luminescence to decrease to baseline. Thus far, signal solutions prepared as described above and stored at 4° C. have maintained their stability for at least six months.

Figure 3:
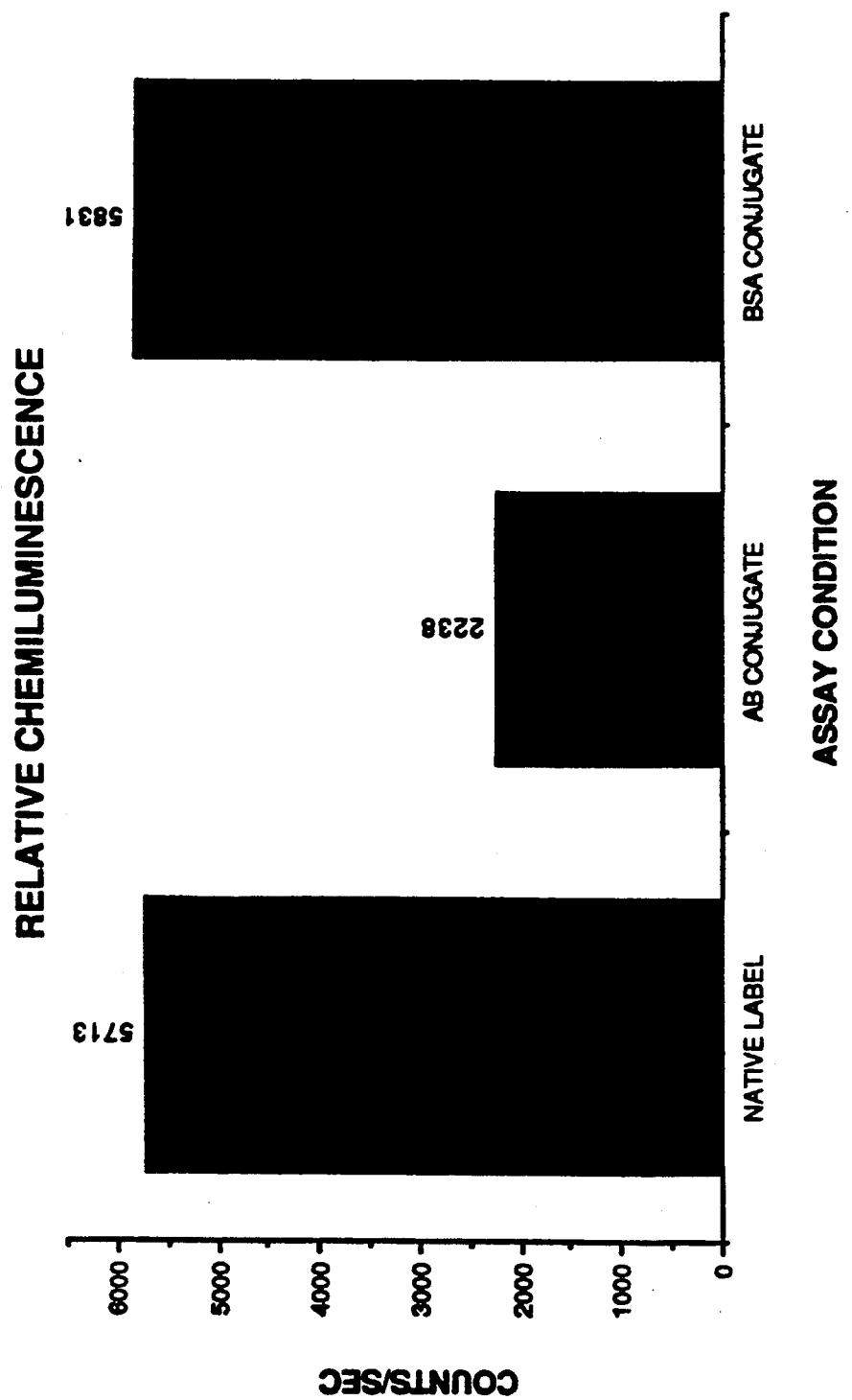
FIG. 3 is a histogram that represents the signal obtained with 100 picomolar concentrations of native DPIX, anti-mouse-DPIX conjugate and estradiol-17$\beta$-BSA-DPIX conjugate.

Examples 2 and 3 showed that the DPIX (without any enzyme/substrate present) triggers a major chemiluminescent reaction at room temperature and that this also occurs following the conjugation of the DPIX label to analytes of interest (FIGS. 2 and 3).

EXAMPLE 4

Assay Comparing DPIX and DPIX Conjugate Fluorescence

Figure 4A:
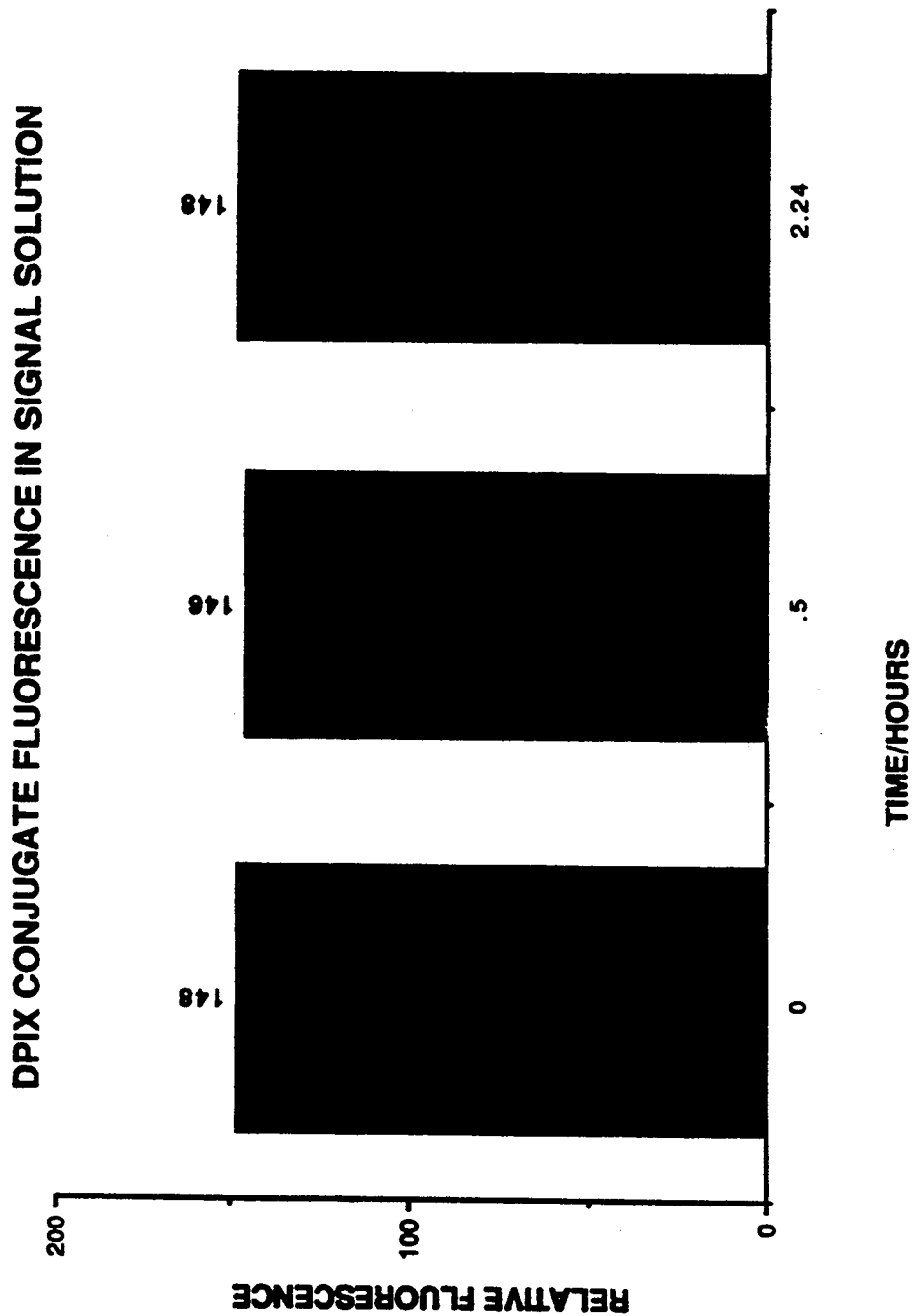
FIGS. 4a and 4b are histograms that represent the lack of change in fluorescence over time with solutions of native DPIX in TSS signal solution and E2-17$\beta$-BSA-DPIX conjugate (1 $\mu$M) in TSS signal solution.
Figure 4B:
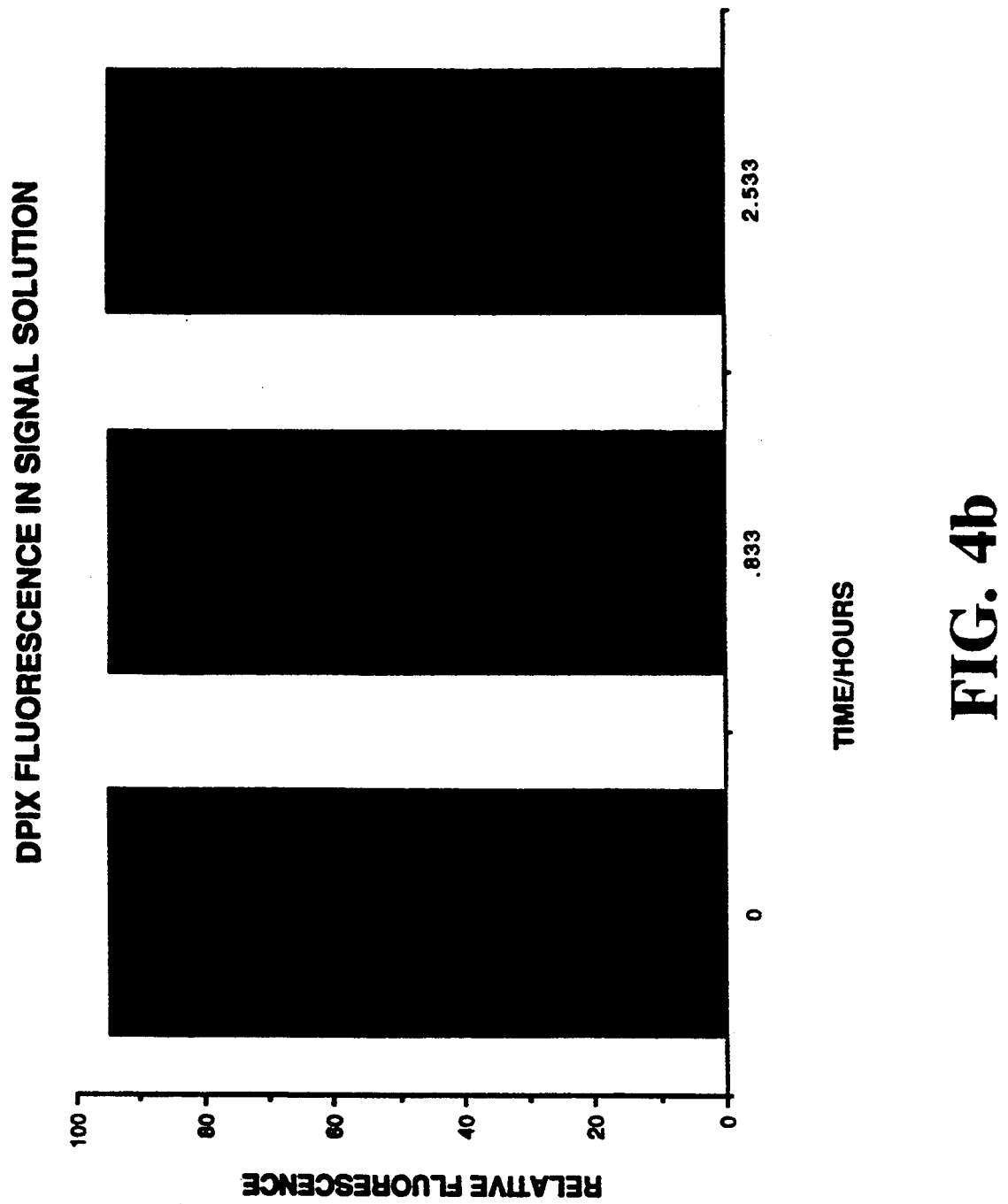

In order to best prove that the nonmetallic tetrapyrrole porphyrin, deuteroporphyrin IX·2HCl (DPIX), used herein did not contain or was not chelating metal ions, fluorescence characteristics of metalloporphyrins and nonmetallic porphyrins were utilized. For example, in some cases the chemical incorporation of metal ions can lead to the formation of nonfluorescent porphyrin molecules. In other cases, such as that of Zn porphyrins, the maximum fluorescence emission is approximately 570 nm with very low emission above 600 nm. The maximum fluorescence of the DPIX in basic aqueous solution is approximately 610 nm. The fluorescence quantum yield of DPIX is approximately 0.1 while the fluorescence quantum yield of Zn porphyrins is approximately 0.04. Therefore, the fluorescent peak measured over time would dramatically decrease and shift to shorter wavelengths if Zn deuteroporphyrin was being formed and an even more dramatic decrease in fluorescence would occur if non-fluorescent metalloporphyrins such as iron porphyrins were formed. Using a Gilford Fluoro IV fluorometer, fluorescent studies of DPIX at a 1 micromolar concentration and an estradiol 17β-BSA conjugate of DPIX (1 μM) in dH$_2$O, in 0.1N NaOH and in a signal solution prepared as in Example 3 were therefore performed. Measurements were taken over several hours and as shown in FIGS. 4a and 4b, the fluorescence did not change in the signal solution, indicating that the DPIX did not contain metal ions and that it did not incorporate metal ions under the conditions supporting a chemiluminescent reaction. This is the best test and support for the claim that nonmetallic tetrapyrrole molecules trigger chemiluminescence.

EXAMPLE 5

Figure 5:
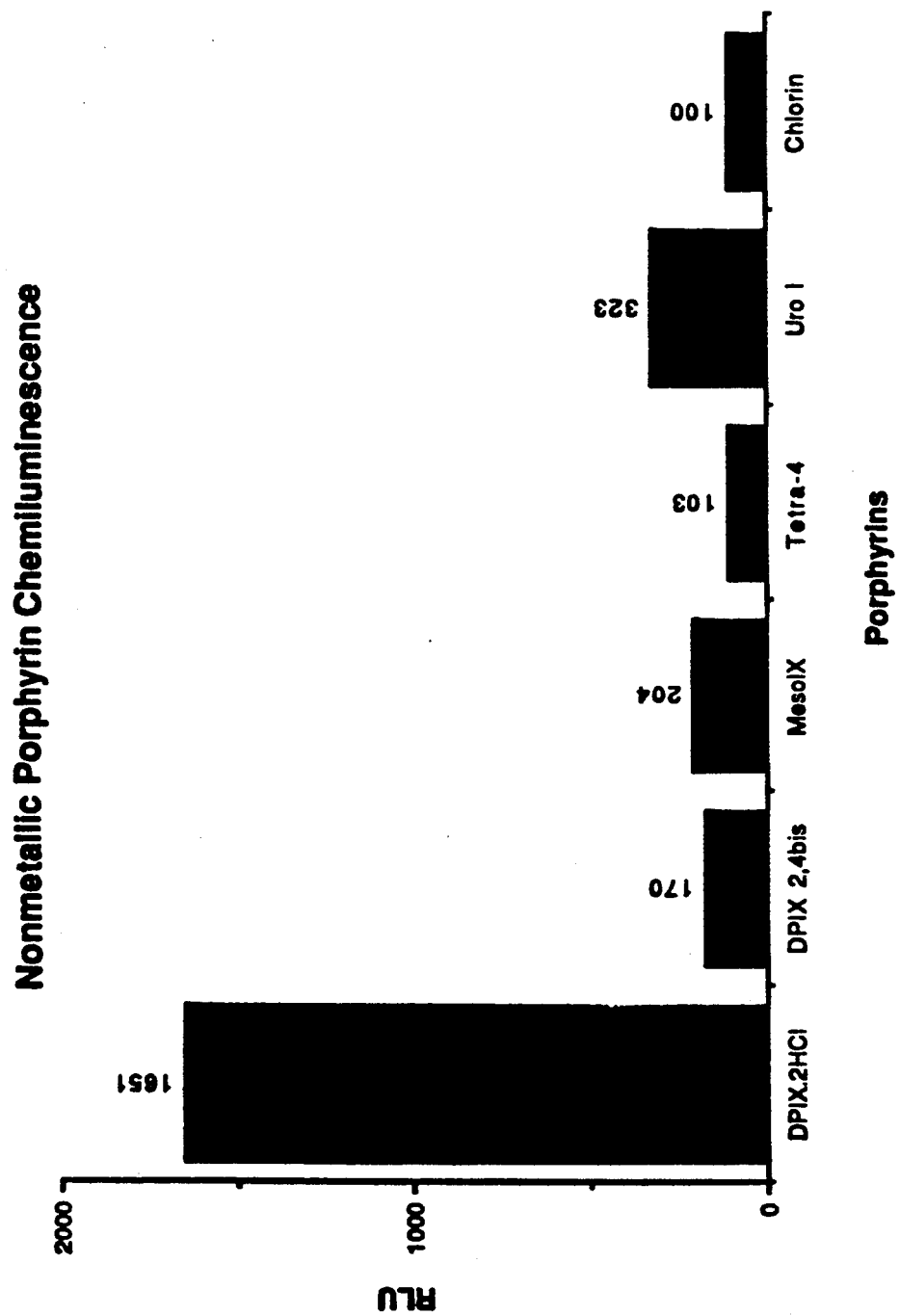
FIG. 5 is a histogram representing relative light outputs from various nonmetallic porphyrin molecules (deuteroporphyrin IX, 2,4 Bis glycol; mesoporphyrin IX dihydrochloride; meso-tetra(4-carboxyphenyl) porphine; uroporphyrin I dihydrochloride and chlorin $e_6$) compared with DPIX.

Assays Comparing the Relative Chemiluminescence of Nonmetallic Porphyrins and Luminescent Reactants Other cyclic nonmetallic porphyrin molecules were tested for their ability to catalyze chemiluminescent reactions and were compared with DPIX. These were: deuteroporphyrin IX, 2,4 bis glycol; meso-tetra(4-carboxyphenyl) porphine; mesoporphyrin IX dihydrochloride; chlorin e$_6$ and uroporphyrin I dihydrochloride (all from Porphyrin Products, Logan, UT). The porphyrin concentration in all cases was 1 micromolar in dH$_2$O and the signal solution was prepared as in Example 3. 35 μl of each porphyrin was flashed with 265 μl of signal solution and the measurements were taken over 1 second in the Berthold Lumat LB 0501 luminometer. FIG. 5 shows the relative light units (RLU) of the other nonmetallic porphyrins compared to DPIX.

Figure 6:
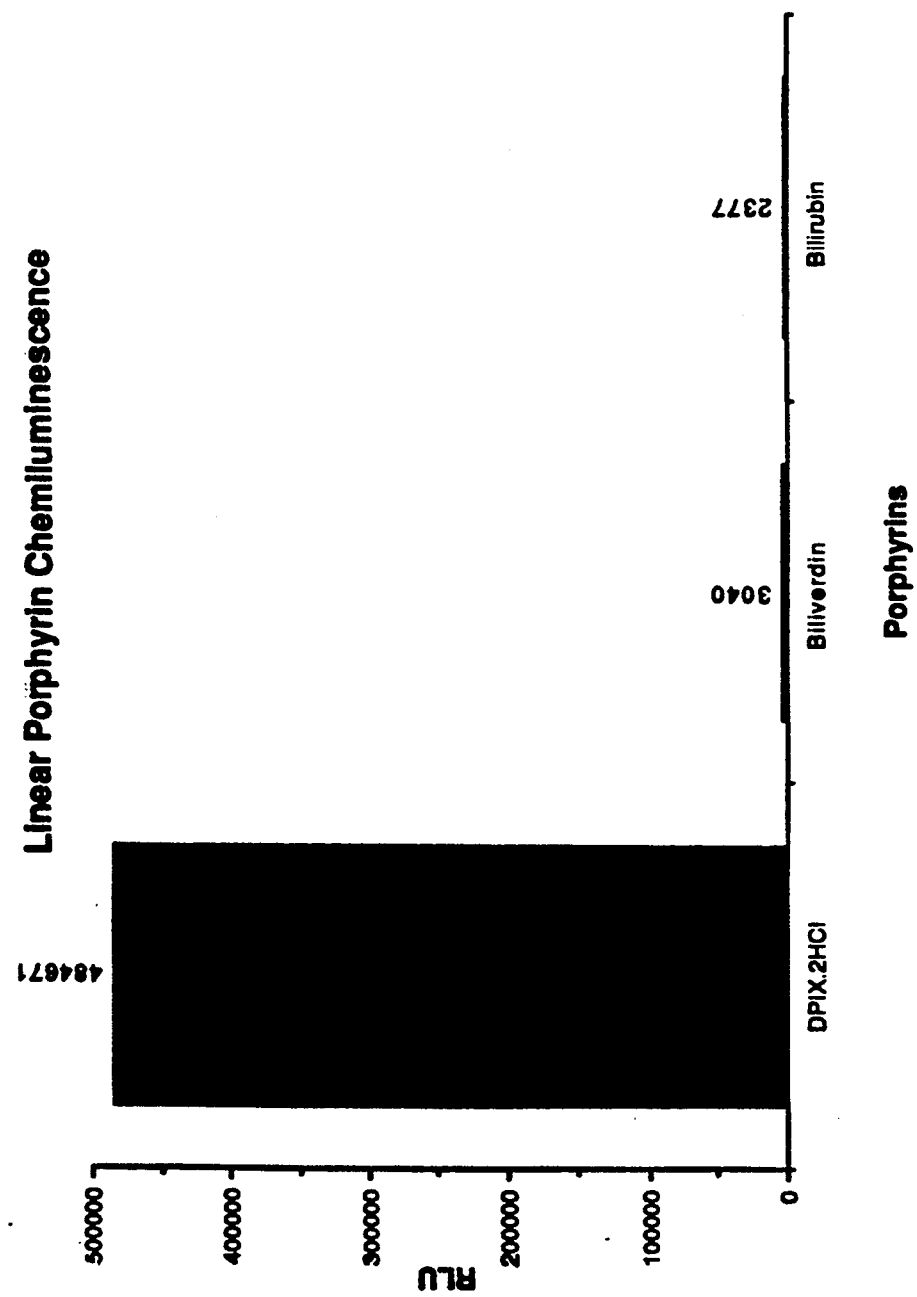
FIG. 6 is a histogram representing relative light outputs from two nonmetallic linear tetrapyrroles compared with DPIX.

The linear nonmetallic tetrapyrroles (bilirubin IX and biliverdin IX hydrochloride) were also tested for their abilities to mediate chemiluminescence and were compared with DPIX, as shown in FIG. 6. The linear tetrapyrroles were dissolved in dH$_2$O and DMSO to a concentration of 1 µM. Otherwise conditions were identical to those used to compare the cyclic nonmetallic porphyrins discussed above.

Figure 7:
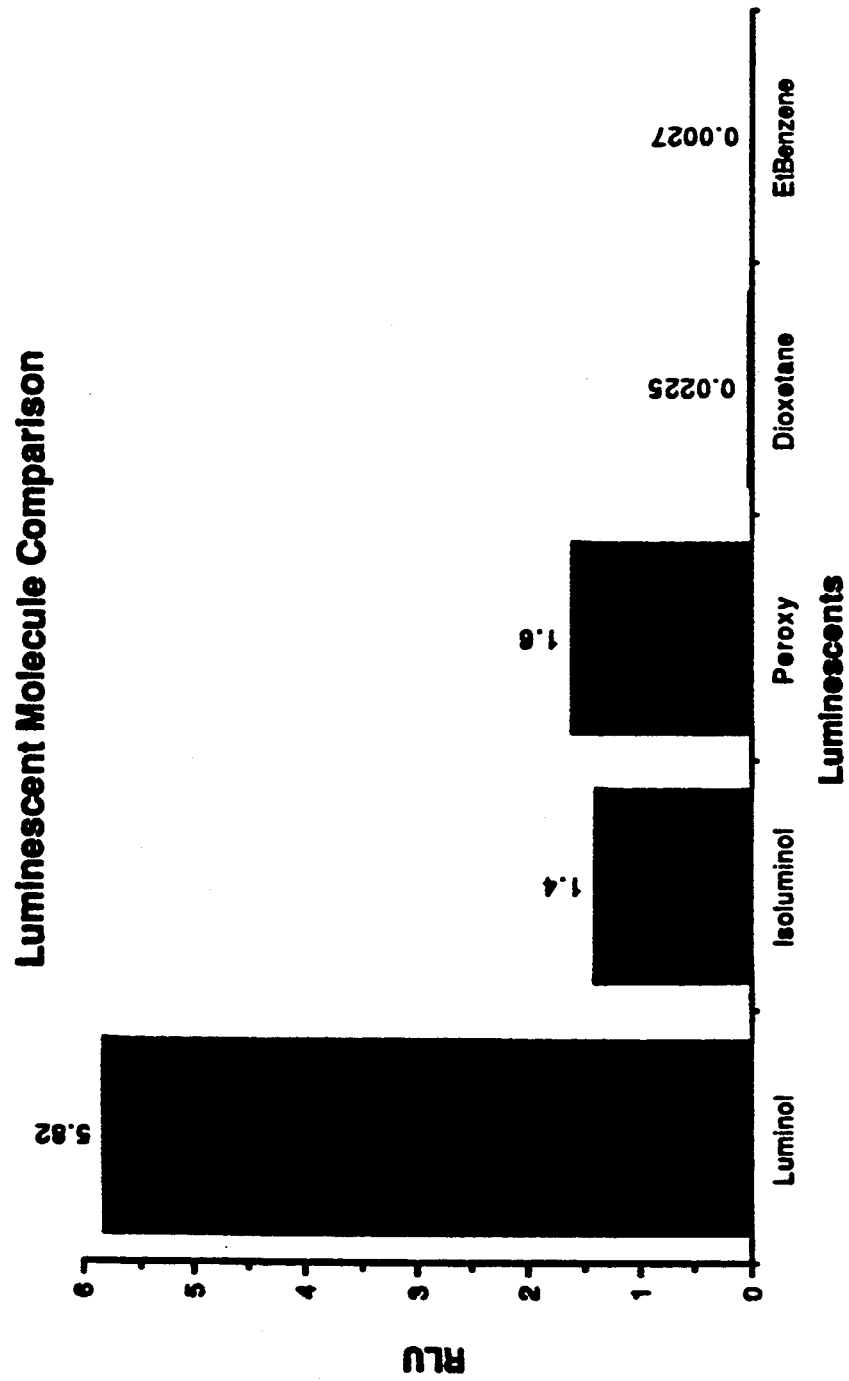
FIG. 7 is a histogram representing relative luminescence produced by various luminescent reactants in the presence of LSS signal solution and DPIX.

Various luminescent/fluorescent molecules which can act as luminescent reactants such as the cyclic diacyl hydrazides (e.g., luminol and N-(4-Aminobutyl)-N-ethyl isoluminol), a peroxyoxylate (2,6-difluorophenyl oxylate), a dioxetane (4-methoxy-4-(3-phosphatephenyl)spirol[1,2-dioxetane-3,2'-adamantane], disodium salt)) and ethylbenzene were also compared as to efficiency of light production when used with oxidants in the presence of the DPIX (FIG. 7). Concentrations of 1 mM/liter of each reactant as a substitution for the luminol of the signal solution prepared as in Example 3 were utilized and 35 µl of DPIX was flashed with 265 µl of signal solution, each with a different luminescent reactant. Otherwise conditions were identical to the cyclic nonmetallic porphyrin comparison described above in this Example. As shown in FIG. 7, the signal solution containing luminol was approximately five times as efficient as the second best solutions containing isoluminol and peroxyoxylate.

EXAMPLE 6

Assay of Deuteroporphyrin IX·2HCl Label in Liquid Phase

A. Preparation of Chemiluminescent Reagents

A 1 mg/ml preparation of nonmetallic tetrapyrrole DPIX (Porphyrin Products) in DMSO was serially diluted in a 0.1 M Trizma base solution in distilled water (dH$_2$O) pH 12.3, containing 28 µl of a 1% solution of sodium di-2-ethylhexyl sulfosuccinate (AOT; K&K Laboratories, Cleveland, OH) per milliliter.

B. Assay Procedure

Figure 8A:
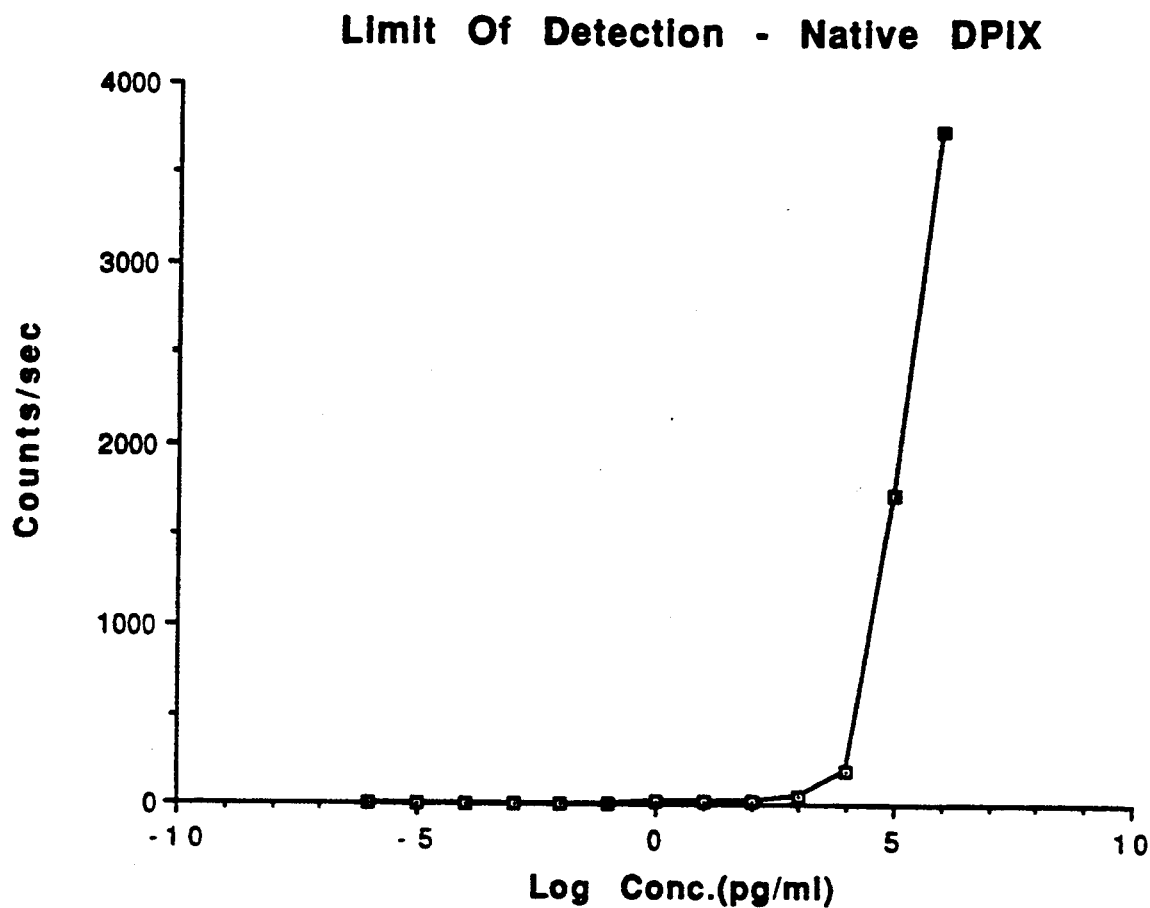
FIGS. 8a and 8b are line graphs demonstrating the limit of detection for DPIX flashed with the TSS signal solution.
Figure 8B:
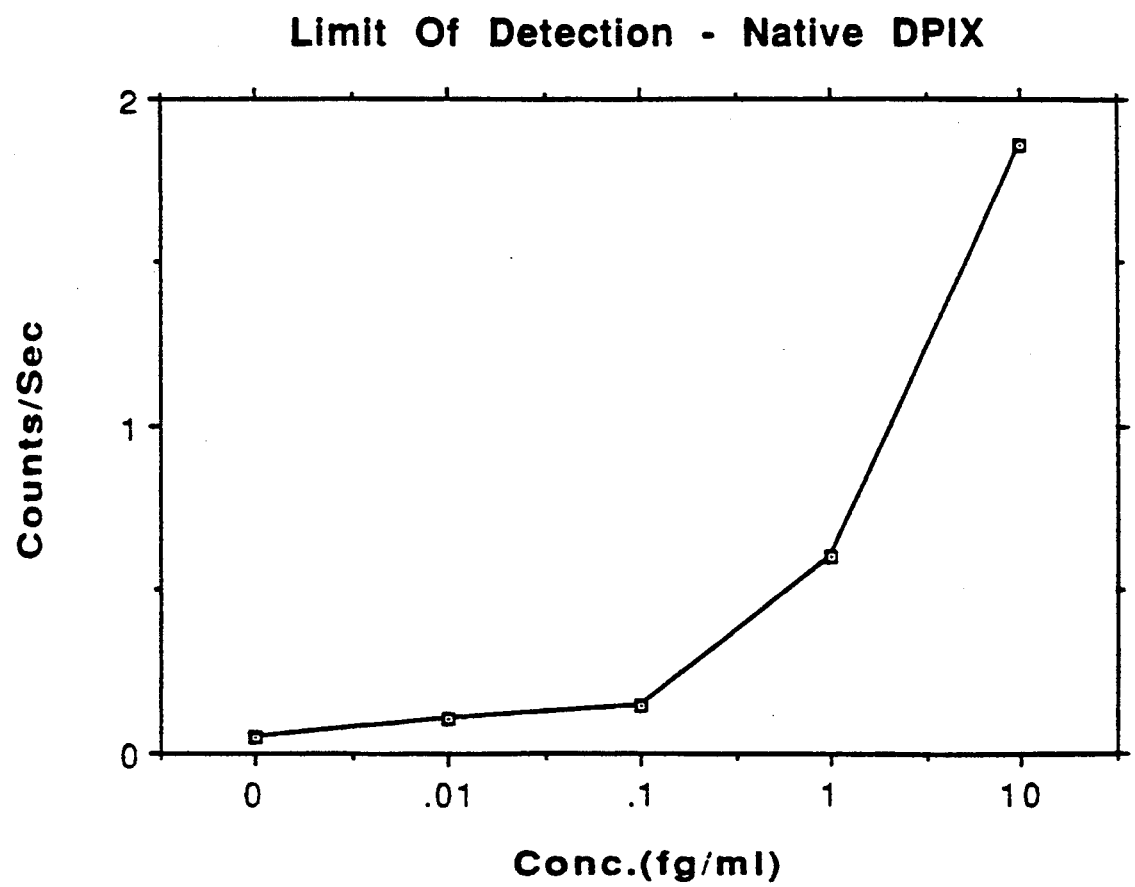

Thirty five microliters of the diluted deuteroporphyrin IX·2HCl (DPIX) was added to a 12×75 mm polystyrene tube and this was followed by the addition of 265 µl of a signal solution prepared as in Example 3. The mixture was vortexed and the tube was read immediately in a manual tube reading Berthold LB 9501 luminometer (Nashua, NH). As shown in FIGS. 8a and 8b, a definite deuteroporphyrin concentration dependent, limit of detection curve was generated which demonstrated ultrasensitive detection in the attomolar (femtogram/ml) range.

C. Kinetics of the Reaction

Figure 9B:
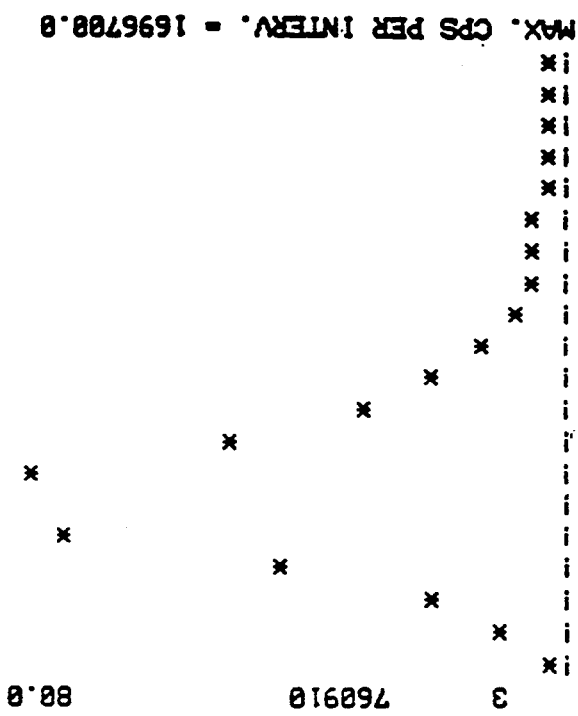
FIGS. 9a, 9b, 9c and 9d are readouts obtained from the Berthold Lumat LB 9501 luminometer.
Figure 9A:
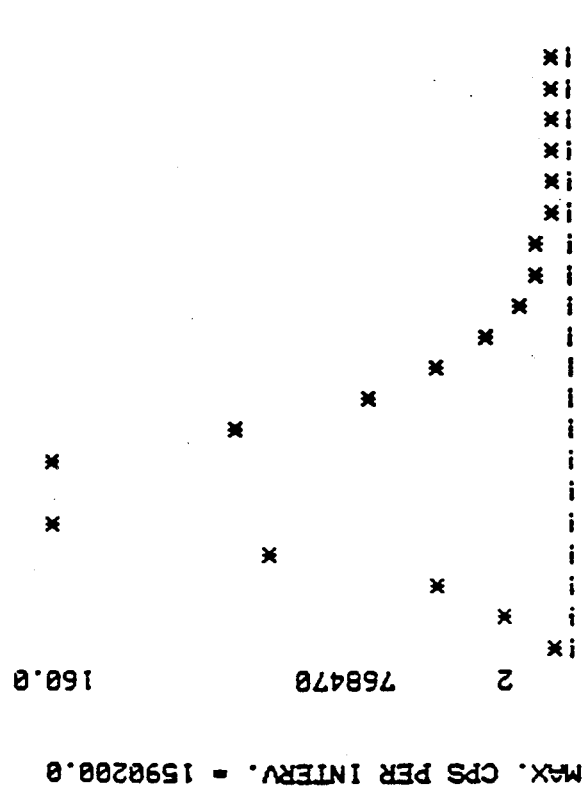
Figure 9D:
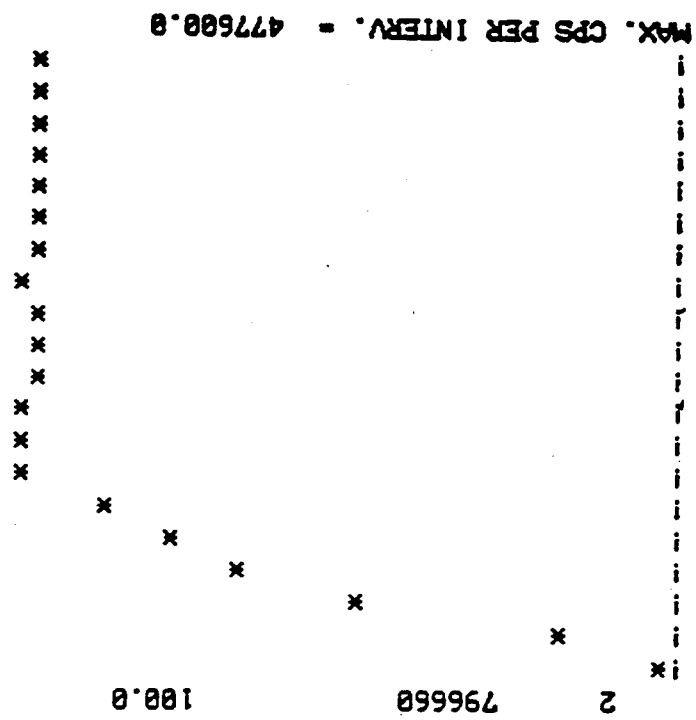
Figure 9C:
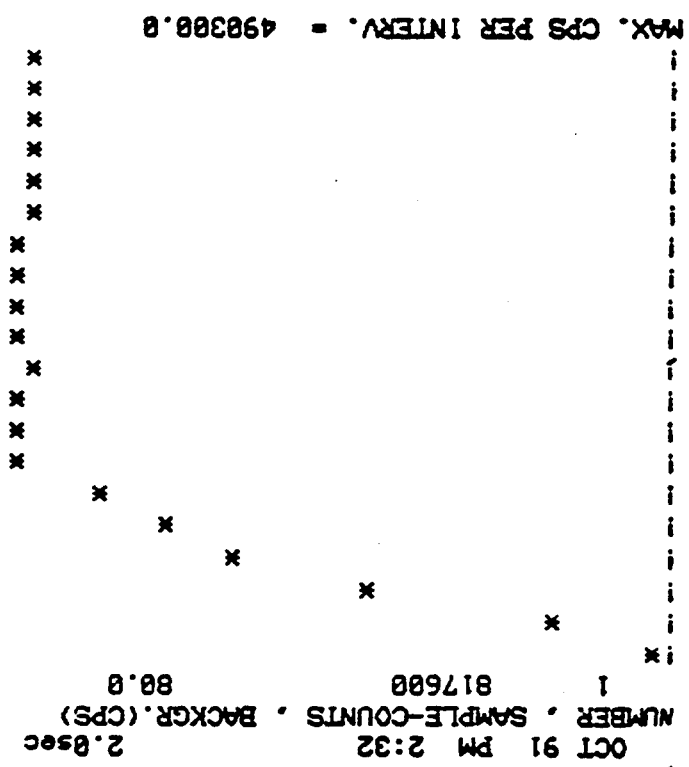

A kinetic study, wherein 20 light output measurements were taken over a period of 2 seconds, demonstrated that the signal solution which produced the maximal light output produced a kinetic curve characterized by a very rapid rise to peak output within 1 second (i.e., 0.6 second), followed by a plateau of output for >1 second (see FIG. 9c and 9d) FIGS. 9c and 9d are repeat measurements of the same sample. This kinetic behavior places tetrapyrrole catalyzed luminescence nearer that of the ~2 to ~5 seconds total time light produced by acridinium derivatives, (Weeks et al., supra.) but these nonmetallic tetrapyrrole molecules produce a longer peak output of light which is easier to capture than the peak or total light output of the acridinium derivatives (compare FIGS. 9a, 9b which show the output of the dimethyl acridinium ester (Ciba Corning, Walpole, MA).

EXAMPLE 7

Solid Phase Assay of Mouse Antibody

A. Preparation of Rabbit Anti-Mouse/Deuteroporphyrin IX·2HCl Conjugate

A two step method of conjugation was utilized. In the first step, dicyclohexylcarbodiimide (DCC, Aldrich) and N-hydroxysuccinimide (NHS, Pierce Chemical Co.) were utilized to produce a stable succinimide ester of DPIX. DPIX has two substituent carboxyl groups which are naturally available for formation of activated NHS esters. DPIX (26 µM or 15 mg) was weighed and dissolved in 1 ml of dimethylformamide. An excess of DCC (37.5 µM or 7.74 mg) and NHS (37.5 µM or 4.3 mg) were added and this solution was stirred for 3 hours at room temperature. During this time some insoluble urea derivatives were formed which were removed by centrifugation for 10 min. at 13,000 rpm. The supernate containing the activated porphyrin ester was stored at 4.0° C. and was used without further purification. The second step involved the conjugation of the activated DPIX porphyrin ester to affinity purified rabbit anti-mouse antibody (Jackson ImmunoResearch Laboratories, Inc., West Grove, Pa.). The molar ratio of porphyrin to antibody can be adjusted by adding more or less of the activated porphyrin on a molar basis. Conjugation was carried out in a mixture of 15% dioxane and 85% phosphate buffer (pH 7.4). Antibody (0,083 µM or 12,465 mg) was added to 1.5 ml of the buffer/dioxane solution. Activated porphyrin was then added (0.25 µM to 5.0 µM) and the mixture was slowly stirred at room temperature for 3 hours. If precipitation occurred, it was removed following centrifugation for 10 minutes at 13,000 rpm. Purification of the conjugate was performed by prepacked Sephadex G-25 (PD-10) column chromatography (Pharmacia). Purified conjugate was stored in amber vials at 4° C. in phosphate buffer (pH 7.4) containing 0.1% sodium azide (NAN3) as a preservative. This conjugate has remained stable for at least 9 months when stored at 4° C.

B. Coating of Solid Phase With Mouse Antibody

Anti-estradiol-17β mouse monoclonal antibody (MAB, Chemicon, El Segundo, CA) was covalently bound to the wells of polystyrene plates (NUNC Covalink, Denmark). These special plates are derivatized in a manner which leaves HN- groups available for the formation of peptide bonds with NHS-ester activated molecules one wishes to covalently bind. Fifteen milliliters of mouse MAB (0.5 µg/ml) plus 0.6 ml of dimethylsulfoxide and 2.76 mg of sulfo-NHS (Pierce) were mixed together to form activated NHS esters. One hundred microliters of this mixture was added in triplicate to each of the six sets of wells and this was followed by 50 µl/well of freshly prepared 6.2 mg/5 ml dH$_2$O of 1-ethyl-3-(3-dimethylaminopropyl)-carbodiimide (EDC, Sigma). The plates were incubated at room temperature for 2 hours and were then dumped and washed 3 times with physiological saline containing 0.5 ml Tween 20/liter. One hundred fifty microliters of 2% BSA containing 0.1% sodium azide was then added into each well for one hour to insure the blocking of unoccupied sites on the wells. Following the blocking, the plate was dumped and the wells were again washed three times.

C. Mouse Antibody Assay Procedure

Figure 10:
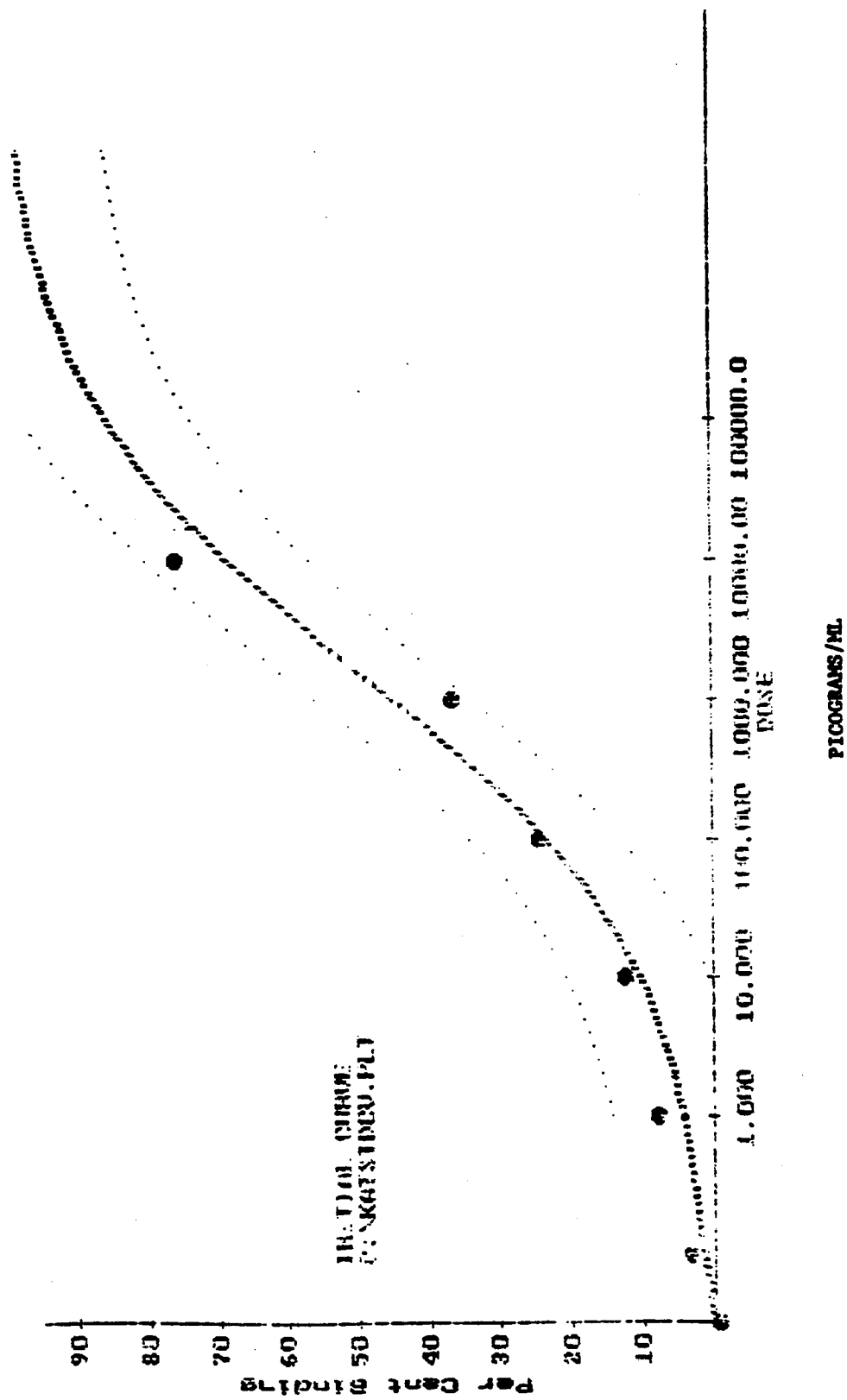
FIG. 10 is a specific binding curve representing the concentration dependent binding of DPIX labeled anti-mouse antibody to covalently bound solid phase mouse monoclonal antibody.

The object of this assay was to determine the degree of specific binding of the deuteroporphyrin IX·2HCl (DPIX) conjugated anti-mouse antibody to covalently bound solid phase mouse monoclonal antibody. The rabbit anti-mouse antibody-DPIX conjugate was initially diluted to a concentration of 100 ng/ml in PBS. The initial triplicate of wells contained this concentration/200 μl of PBS. Subsequent triplicates of wells contained 1:10 dilutions of the conjugate with a final concentration of 1.0 pg/ml. Positive controls consisted of the addition of 1 μg/ml of conjugate to 2 antibody bound wells and the zero controls consisted of the addition of 1 μg/ml of conjugate to 2 wells containing no antibody. The plates were then incubated for 1 hour at room temperature, were washed three times and tapped dry. This was followed by the addition of 200 μl of signal reagent to the wells and reading of the plate in the Dynatech ML 1000 plate luminometer. FIG. 10 shows the concentration dependent specific binding curve of DPIX labeled anti-mouse antibody to solid phase covalently bound mouse monoclonal antibody.

EXAMPLE 8

Assay of DPIX-BSA-Estradiol-17βConjugate in Liquid Phase

A. Preparation of Reagents

The sample nonmetallic deuteroporphyrin IX·2HCl-BSA-estradiol-17β2 conjugate was prepared after the procedure for DPIX conjugate preparation described in Part A of Example 7. The conjugate was then serially diluted in a 0.1 M Trizma base solution in distilled water (dH2O, pH 10.3). The signal solution was prepared as described in Example 3 above.

B. Assay Procedure

Figure 11:
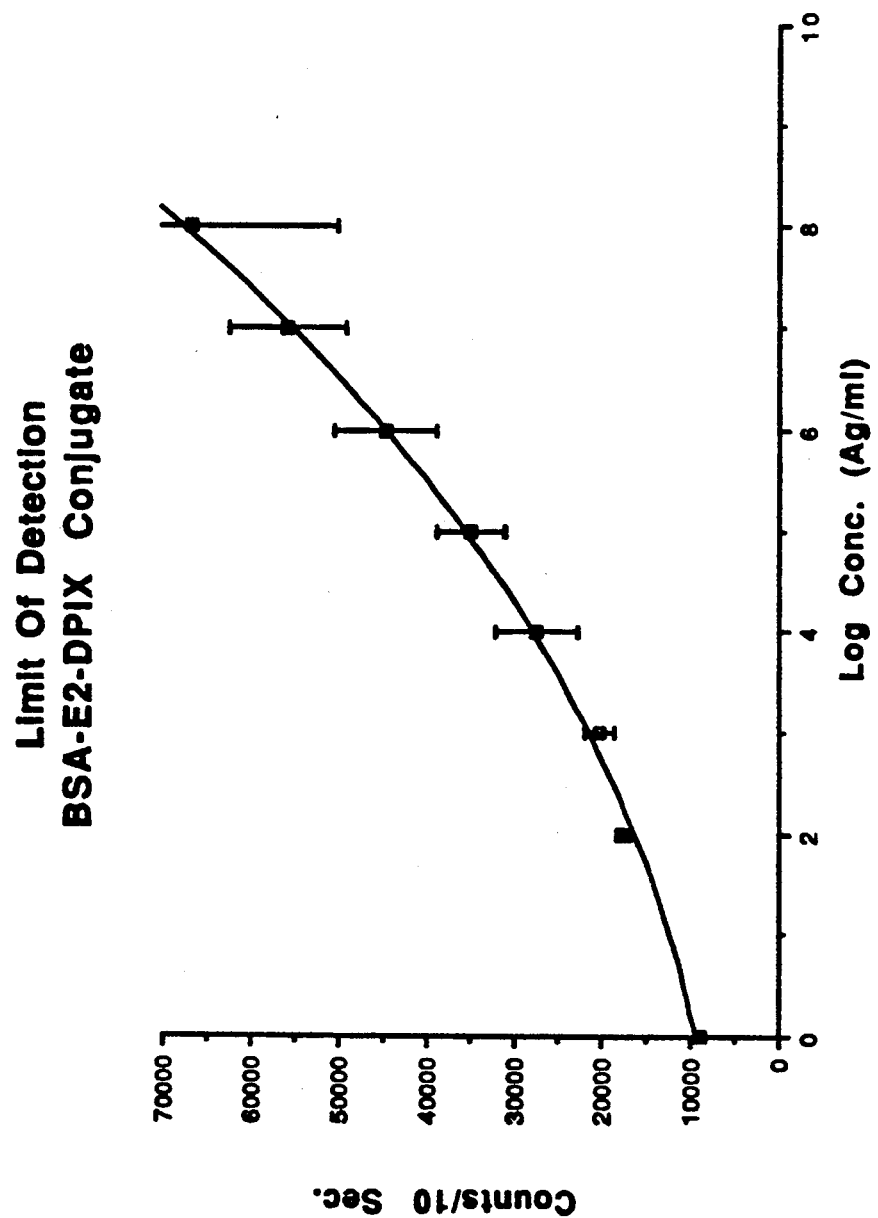
FIG. 11 is a limit of detection curve demonstrating the sensitivity of detection for the BSA-E2-17$\beta$-DPIX conjugate in the subattomolar (10-19) range (the first point represents a 2X signal over zero).

Thirty five microliters of the diluted deuteroporphyrin IX·2HCl conjugate was added to a 12×75 mm polystyrene tube and this was followed by the addition of 265 μl of the signal solution prepared in paragraph A above. The mixture was vortexed and the tube was read immediately in a manual tube reading EG+G Berthold LB 9501 luminometer (Nashua, NH). As shown in FIG. 11, a definite deuteroporphyrin concentration dependent limit of detection curve was generated which demonstrated ultrasensitive detection in the $1 \times 10^{-19}$ molar range C. Kinetics of the Reaction A duplicate kinetic study with this DPIX conjugate demonstrated that the signal solution yielding kinetic curves characterized by a very rapid rise to peak output within 1 second, followed by a plateau of output for >1 second (FIG. 9c, 9d).

EXAMPLE 9

Use of Deuteroporphyrin IX·2HCl with Acridinium Derivative

Sequential Flashing of an Acridinium Derivative and DPIX

Phenyl 9-acridinecarboxylate (98%, Aldrich) was the acridinium derivative used in this example. This derivative was found to be nearly insoluble in aqueous environments but soluble in the three organic solvents tried: dimethylformamide (DMF), dimethylsulfoxide (DMSO) and isopropyl alcohol. When 100 μg (10 μl of derivative) was dissolved in DMF, the DMF would react with polystyrene tubes to produce a milky white opacity. It was necessary to add 10 μl of the derivative in DMF to 100 μl of dH2O to prevent opacity. The concentration of derivative was 100 μg/10 μl pipetted into each tube. DPIX (Porphyrin Products, Logan, UT) was initially dissolved in DMSO at a concentration of 1 mg/ml. This was further diluted in 0.1 M Trizma base in dH2O to a final concentration of 100 ng/ml. The DPIX preparations futher used in this Example consisted of 35 μl/tube of this 100 ng/ml dilution.

Figure 12:
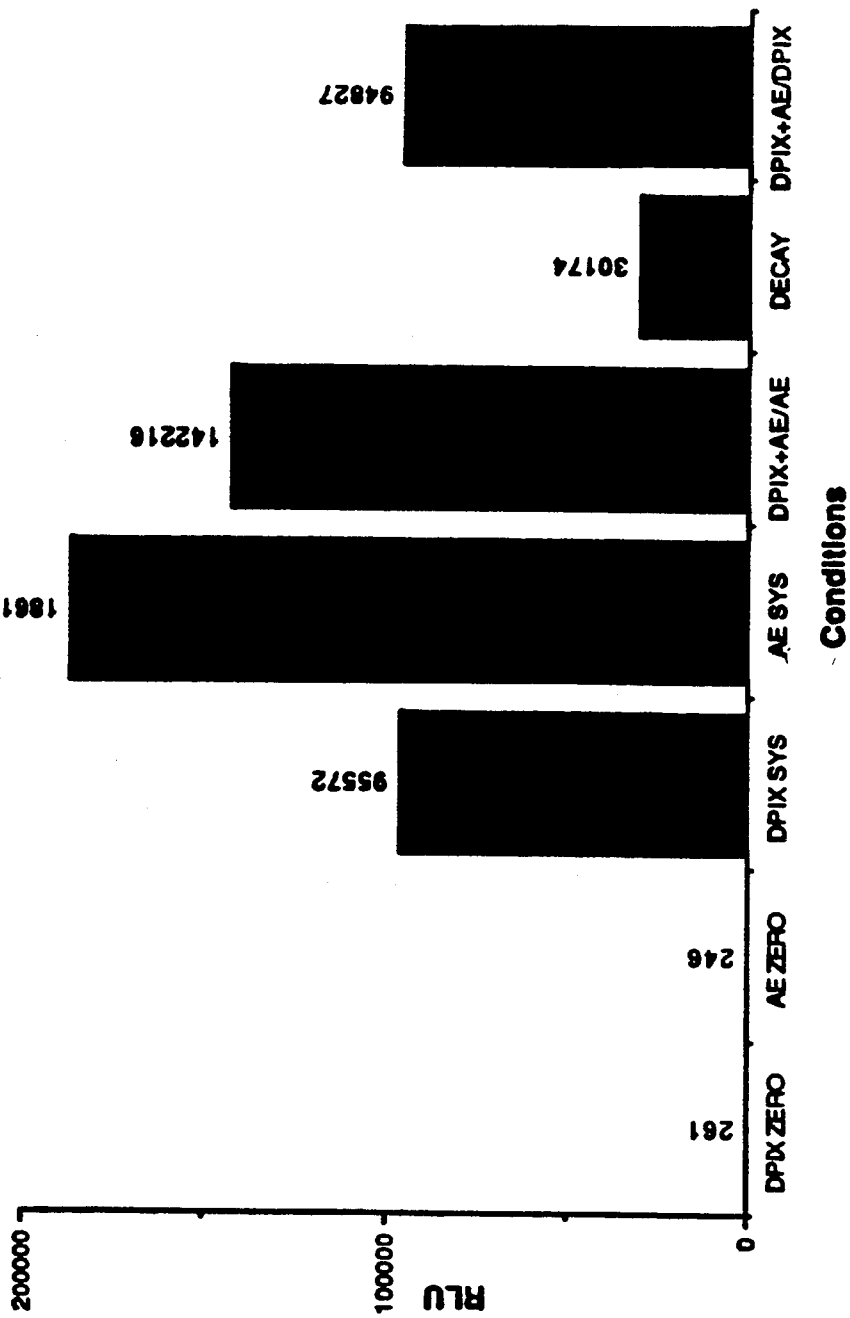
FIG. 12 is a histogram demonstrating the feasibility of combining DPIX and an acridinium derivative (phenyl 9-acridinecarboxylate (Aldrich) designated as "AE"0 in this Figure but also designated "AD" in the examples) and sequentially flashing the two label systems with different respective signal solutions. Bar 1 is TSS minus DPIX (zero); Bar 2 is AD signal solution ($H_2O_2$+NaOH) minus AE; Bar 3 is 10 ng DPIX flashed with TSS; Bar 4 is 10 ng AE flashed with $H_2O_2$+NaOH; Bar 5 is the flashing of a mixture of 10 ng DPIX+10 ng AE with $H_2O_2$+NaOH followed by decay (Bar 6); Bar 7 is the subsequent flashing of DPIX in the mixture with TSS.
Figure 13:
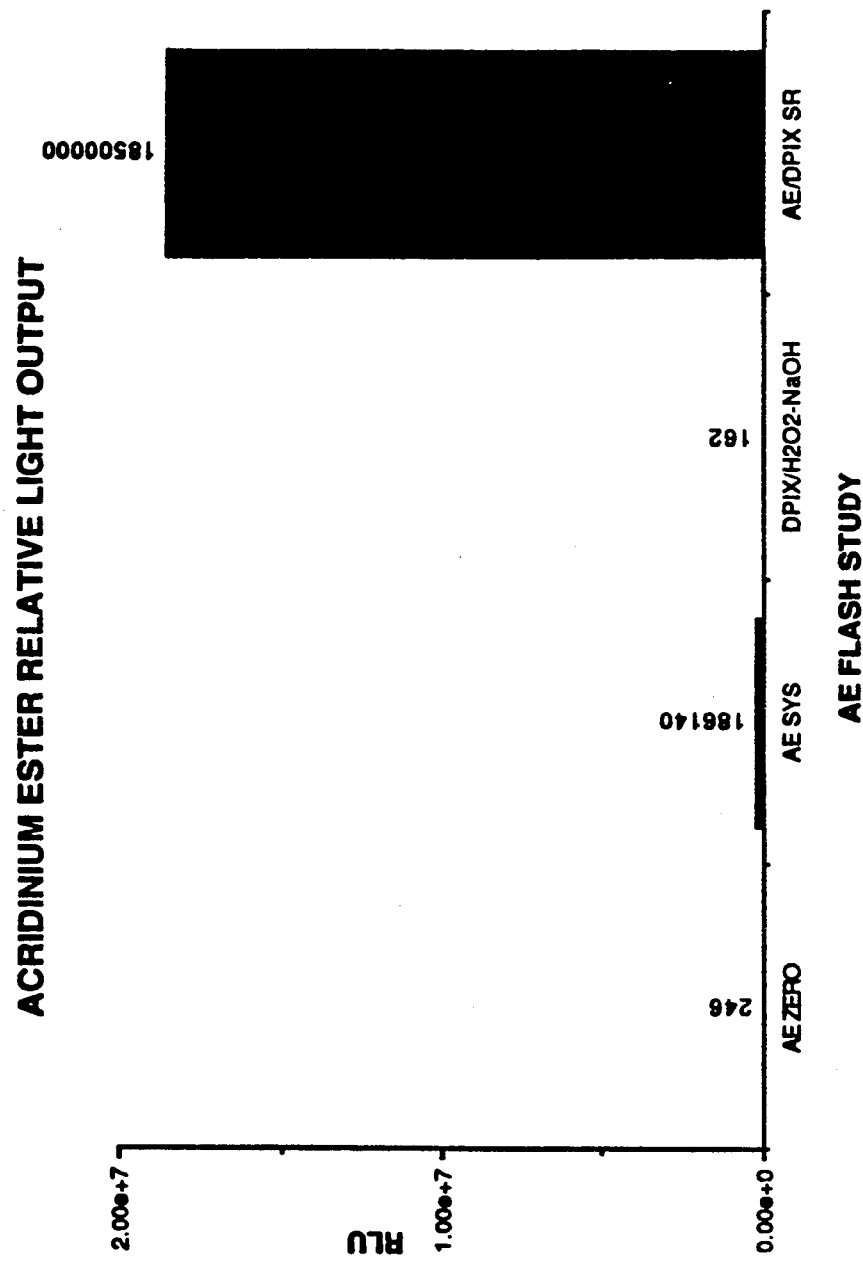
FIG. 13 is a histogram showing the amplification of the light output by an acridinium derivative (phenyl 9-acridinecarboxylate) when flashed with LSS signal solution. The bar designated "AE SYS" represents the acridinium derivative flashed with $H_2O_2$ followed by NaOH. The bar designated "AE/DPIXSR is the same AE derivative flashed in the LSS signal solution."

There were 3 signal solutions used in this Example. The first was prepared according to Example 3 and was used to flash DPIX. Two other separate solutions H2O2-HNO3 (R1) and NaOH (R2) were used to flash the acridinium derivative. These were prepared according to Sturgess, M.L., et al., Clin. Endocrin., .2.7:383-393 at 385 (1987). The results showed that DPIX could not be flashed by the sequential addition of 1.5% H2O2 in 0.1 M HNO3 (R1) (300 μl) and 0.25 M NaOH (R2) (300 μl) signal solutions used for the derivative (FIG. 13, Bar 3). FIG. 12 shows the results of the experiment which compared the performance of the DPIX system (Bar 3), AD system (Bar 4) and the results of combining the acridinium derivative and DPIX and sequentially flashing the combined label systems with their respective signal solutions (i.e., a tube to which 35 μl DPIX and 10 μl AD in 100 μl H2O were added was first flashed by sequential addition of R1 and R2 (Bar 5)). Bar 6 is the signal after 5 sec. decay and Bar 7 is the signal obtained from DPIX when the Example 3 signal solution was added to the same tube already containing R1 and R2. This experiment and result was repeated with the anti-mouse antibody-DPIX conjugate prepared in Example 7. It was also noted that when the luminescent reactant luminol was removed from the formulation of the signal solution, a decrease in background counts of approximately 10 fold was seen when flashing the acridinium derivatives and lucigenin (See Table 1, infra.). Another very interesting finding was the production of a strong signal (100 times that seen when flashing with R1 followed by R2 as shown in FIG. 13, Bar 2) when the acridinium derivative was dissolved in DMF and 15 μl of a 1 mg/ml solution was mixed with 100 μl dH2O and subsequently flashed with the LSS signal solution (see FIG. 13, Bar 4). It was subsequently demonstrated that the kinetics of this LSS signal solution reaction converted from the acridinium derivative conjugate anti TSH-dimethylacridinium ester flash-type reaction seen with the R1+R2 combination (FIGS. 9a and 9b) to a glow-type (>5 sec.) lasting longer than 1 minute (see FIGS. 14a and 14b).

EXAMPLE 10

Comparison of NaOH Containing Signal Solutions

This example compared the performances of two solutions containing NaOH which were used to flash several luminescent labels. Equal amounts of 1.5% H2O2 in 0.1N HNO3 and 0.25N NaOH were mixed to form one solution. The performance of this solution was compared with one containing 0.035 ml of 200 mM KO2/ml of dH2O with the pH adjusted to 12.48 with 1N NaOH to give the following relative light outputs as measured on a Berthold luminometer:

|   | (H$_2$O$_2$ + NaOH) | (KO$_2$ + NaOH) |
|---|---|---|
| A.E.-antiTSH conjugate | 181 | 725 |
| Lucigenin | 979 | 847 |
| X.O. | 3 | 73 |
| Luminol | 290 | 882 |
| Luciferin | 17 | 34 |
| DPIX | 103 | 213 |
| Zero | 24 | 16 |

These outputs were obtained by flashing 10 microliters of 1 μM concentrations of each luminescent molecule in dH$_2$O with 600 microliters of each signal solution and read for 10 seconds. The 4-(2-succininidyloxycarbonyl-ehtyl)phenyl 1-10-methyl acridinium-9-carboxylate fluorosulfonate acridinium derivative (A.E.) anti-TSH conjugate was obtained from London Diagnostics, Eden Prarie, MN. The DPIX was obtained from Porphyrin Products, Logan, UT. The xanthine oxidase (X.O.) was obtained from Sigma, St. Louis, MO.

EXAMPLE 11

Assays Comparing the Performance of Various Luminescent Molecules with Different Signal Solutions A. The luminescent molecules used in this assay were phenyl 9-acridinecarboxylate (A.D.) (98%, Aldrich); lucigenin (Sigma) xanthine oxidase (X.O.) (Sigma); luminol (Sigma); luciferin (Sigma); and deuteroporphyrin 1X·2HCl (DPIX) (Porphyrin Products). A volume of 10 μl of each of these luminescent molecules, all at a concentration of 1 μg/ml, were flashed respectively with 265 μl of the following signal solutions: a novel signal solution at pH 12.85 prepared according to Example 3 (SS+Lum); the same signal solution as in Example 3 at pH 12.06 but without luminol (SS); a solution containing sodium-perborate, hypoxanthine, luminol and Fe-EDTA in a borate buffer at pH 10.2 prepared according to A. Baret and V. Fert, *J. Biolum. Chemilum.*, 4:149–153 at p. 151 (Column 1, line 1–4) (1989) but without the xanthine oxidase enzyme; a solution containing H$_2$O$_2$ in HNO$_3$ (R1) followed by NaOH (R2) at a pH of 12.0 prepared according to M.L. Sturgess, et al., *Clin. Endocrin.*, 27:383–393 at p. 385 (1987) (H$_2$O$_2$/NaOH); a solution of 20 mM KO$_2$ titrated to a pH of 12.48 by the addition of 10 M NaOH; and the above "Baret" solution plus 350 μl/ml of the above "KO$_2$" solution (Baret+KO$_2$). Table 1 below shows the counts obtained for 10 seconds÷100 on the Berthold LB 9501 luminometer.

B. An assay similar to the one in paragraph A was done using the acridinium derivative 4-(2-succinimidyloxycarboxyethyl)phenyl 1-10-methylacridinium-9-carboxylate fluorsulfonate (London Diagnostics, Eden Prarie, MN) (A.E.-NHS), the lucigenin, luminol, luciferin and DPIX described in paragraph A above as well as combinations of lucigenin+luminol, DPIX+lucigenin, luciferin+luminol and A.E.-NHS+lucigenin. An amount of 10 μl at 1 μg/ml of each of these luminescent molecules and 5 μl of each molecule (1 μg/ml) where combinations were used were flashed with 265 μl of the "SS" signal solution in paragraph A above (i.e., the signal solution of Example 3 without luminol). Counts were obtained for a period of 60 seconds and are shown in Table 2 below. Otherwise the conditions were identical to those described in paragraph A.

TABLE 2

Evidence for Simultaneous Flashing of Lucigenin and Acridinium Derivatives

| Molecules | Counts/60 Sec. |
|---|---|
| A.E.-NHS | 108233 |
| Lucigenin | 72295 |
| Luminol | 23240 |
| Luciferin | 640 |
| DPIX | 2334 |
| Lucigenin + Luminol | 1197867 |
| DPIX + Lucigenin | 1114211 |
| Luciferin + Luminol | 50752 |
| A.E.-NHS + Lucigenin | 173647 |
| Zero | 100 |

C. A third comparison assay similar to those in paragraphs A and B was done using DPIX at 1 μM in dH$_2$O otherwise prepared according to paragraph A; coenzyme A; horseradish peroxidase (HRP); bovine serum albumin (BSA); horse serum albumin (HSA); vitamin B$_{12}$; and the metallic porphyrin containing molecules, cytochrome C and hemoglobin. All of these respective molecules were obtained from Sigma Chemical Co., St. Louis, Mo. An amount of 10 μl of a 1 μM dilution in dH$_2$O of each of the above molecules was flashed in 265 μl of the "SS+Lum" "Baret" and "Baret+KO$_2$" signal solutions described in paragraph A. Counts were obtained for a period of 30 seconds and are shown in Table 3. Otherwise conditions were identical to those described in paragraph A. The high light outputs seen when flashing the luminescent molecules with the Baret and KO$_2$ solution are due to the augmentation of signal produced by the presence of the additional luminescent molecule hypoxanthine.

TABLE 1

Relative Performance Comparisons Of Various Luminescent Molecules When Flashed With Separate Signal Solutions (Counts/10 sec. ÷ 100)

| Molecules | Signal Solutions | | | | | |
|---|---|---|---|---|---|---|
|  | SS + Lum | SS | Baret | H$_2$O$_2$/NaOH | KO$_2$ | Baret + KO$_2$ |
| A.D. | 303 | 185000 | 2 | 1820 | 336 | 498 |
| Lucigenin | 2734 | 69032 | 1 | 1934 | 374 | 903 |
| X.O. | 190 | 3 | 600 | 8 | 5 | 2514 |
| Luminol | 88 | 232 | 1 | 737 | 1989 | 1144 |
| Luciferin | 127 | 2 | 1 | 32 | 3 | 125 |
| DPIX | 2630 | 1 | 2 | 4 | 51 | 9882 |
| Isoxanthopterin | 40 | 99 | 1093 | 66 | 6 | 33747 |
| Hypoxanthine (6-hydroxypurine) | 123 | 240 | 899 | 458 | 247 | 21601 |
| Zero | 9 | 1 | 1 | 2 | 5 | 460 |

TABLE 3

| Molecules | Signal Solutions | | |
|---|---|---|---|
| | SS + Lum | Baret | Baret + KO$_2$ |
| DPIX | 546,580 | 14,698 | 1,036,019 |
| Coenzyme A | 8,843 | 65,241 | 112,614 |
| HRP | 608,859 | 114,242 | 1,179,102 |
| BSA | 43,425 | 223,695 | 599,330 |
| HSA | 54,810 | 235,165 | 582,740 |
| B12 | 30,496 | 68,319 | 216,896 |
| Cytochrome C | 432 | 90 | 710 |
| Hemoglobin | $2.414 \times 10^9$ | 177,431 | $1.78 \times 10^{10}$ |
| Zero's | 3,143 | 24,851 | 60,877 |

EXAMPLE 12

Use of Deuteroporphyrin IX·2HCl as a Label in a Nucleic Acid, Nonradioactive Measurement of Hybridized Nucleic Acids This measurement process involves three basic steps. In the first, a biotin-labeled probe is hybridized to the membrane immobilized nucleic acid. The second is marked by streptavidin-DPIX conjugate binding to the biotin groups and in the third, the solid phase is incubated with signal solution which mediates the chemiluminescence. Alternatively DPIX can be biotinylated and added to the streptavidin bound intermediate. The emitted light is then detected on photographic film.

A. Preparation of Biotinylated Probe

The BIOPRIME DNA Labeling System (GIBCO BRL, Gaithersburg, MD) is used for the production of biotinylated DNA probes. In this method, random primers (octamers) are annealed to the denatured DNA templates (i.e., ampicillin resistance gene) and these are extended by Klenow fragment in the presence of biotin-14-dCTP to produce the biotinylated probes. Specifically, 100 ng DNA is denatured by dissolving it in 5–20 μl of dilute buffer in a microcentrifuge tube and heating for 5 min. in a boiling water bath followed by immediate cooling on ice. With the denatured DNA still on ice 5 μl of 10X dNTP mixture (1 mM biotin-14-dCTP; 1 mM dCTP; 2 mM dATP; 2 mM dGTP; 2 mM dTTP in 10 mM Tris-HCl, pH 7.5, 1 mM Na$_2$EDTA), 20 μl 12.5X random primers solution (125 mM Tris-HCl, pH 6.8) and dH$_2$O to a total volume of 49 μl are added and briefly mixed. Then 1 μl of Klenow fragment (40 units/μl of the large fragment of DNA polymerase I in 100 mM potassium phosphate buffer (pH 7.0), 10 mM 2-mercaptoethanol and 50% (v/v) glycerol) is added followed by gentle but thorough mixing. This is then centrifuged at 10,000 rpm for 15–30 sec. and incubated at 37 C. for 60 minutes. The reaction is then stopped by adding 5 μl of stop buffer (0.2 M Na$_2$EDTA, pH 7.5). The unincorporated nucleotides are separated from biotinylated DNA probes by column chromatography utilizing a 0.5 cm×5.0 cm column of Sephadex G-50 equilibrated with TE buffer [10 mM Tris-HCL (pH 7.5) in 1 mM Na$_2$EDTA]. Fractions are collected and 1 μl from each fraction is spotted on nylon membrane (PhotoGene, GIBCO BRL). The membranes are then baked for 1 hr. in an 80 degree vacuum oven and the peaks of biotinylated DNA are determined by addition of the BRL PhotoGene nonradioactive detection system. The peak fractions are then combined.

Southern Blot Using Deuteroporphyrin IX·2HCl Label

To provide a control for activity of the testing reagents, biotinylated ampicillin resistance DNA is serially diluted from 10 pg/ml to 0.1 pg/ml in DNA dilution buffer (0.1 μg/ml herring sperm DNA in 6×SSC (0.9 M NaCl; 0.09 M sodium citrate dihydrate, pH 7.0)). Ten 1×5 cm nylon strips are then cut and marked into 1 cm squares. Biotinylated DNA (5 μl) from each dilution is then spotted sequentially onto each strip. The final square on each strip is spotted with DNA dilution buffer as a negative control. The control strips are then dried in a vacuum oven for 1 hr at 80° C. The DNA strips are then wet and washed with TBS-Tween 20 (100 mM Tris base, 150 mM NaCl, 0.05% Tween 20, pH 7.5). The membranes are then blocked by gently agitating for 1 hour at 65° C. in a covered plastic container with blocking solution (3 gm BSA in 100 ml TBS-Tween 20, pH 7.5). Deuteroporphyrin IX·2HCl is then conjugated to streptavidin after the method of Example 7. This streptavidin-DPIX conjugate is then microcentrifuged for 4 min. and 7 μl/100 cm$^2$ of conjugate is diluted 1:1000 in TBS-Tween 20 under sterile conditions. The membranes are then submersed and incubated under gentle agitation with the conjugate dilution for 10 min. at room temperature. The membranes are washed twice for 15 min. with TBS-Tween 20. They undergo a final 1 hr wash with gentle agitation in PBS containing 0.5% Tween 20. The membranes are then blotted on 3 MM filter paper and are again submerged in a signal solution and are immediately exposed to XAR film (Kodak, Rochester, N.Y.). A signal solution prepared according to Example 3 is preferred but other signal solutions such as one containing KO$_2$ and a luminescent reactant (i.e., luminol), or a combination of KO$_2$, BTAH, TNP, cumene hydroperoxide and a luminescent reactant may also be used. The length of time for exposure is 1 min. at room temperature. In performing the southern blots for the unknowns, agarose gel electrophoresis and DNA transfer to nylon membrane are performed by standard techniques [Maniatis, T. et al., Molecular Cloning: A Laboratory Manual (Cold Spring Harbor Laboratory, Cold Spring Harbor, N.Y.):383 (1982)]. Following filter paper and membrane drying, a commercial hybridization system (BioNick, Gibco BRL) is employed for labeling a plasmid containing a double stranded ampicillin resistance gene with biotin-14-dATP by nick translation. After preparation of the probe, the hybridization is performed by prehybridizing the membranes for 3 hrs at 42° C. in plastic bags submerged in 250 μl of prehybridization solution/cm$^2$ of membrane surface area (prehybridization solution: NaCl 0.9 M, NaH$_2$PO$_4$·H$_2$O 0.06 M, Na$_2$EDTA. 2H$_2$O 0.006 M, Ficoll 0.1% (w/v), polyvinylpyrrolidone 0.1% (w/v), BSA 0.1% (w/v), SDS 1.0% (w/v) in 40 ml dH$_2$O; pH to 7.4 with 4 M NaOH and add 2.0 ml 10 mg/ml sheared, denatured salmon sperm DNA; adjust volume to 50 ml with dH$_2$O and add 50 ml formamide). The amount of probe is calculated by the formula: area of membrane in cm$^2$×50 ng probe/ml×0.1 ml/cm$^2$ membrane=ng of probe. The probe is then ethanol precipitated and dissolved in 50 μl of 2X hybridization buffer per cm$^2$ (NaCl 1.8 M, NaH$_2$PO$_4$·H$_2$O 0.12 M, Na$_2$EDTA·2H$_2$O 0.012 M, ficoll 0.2% (w/v), polyvinylpyrrolidone 0.2% (w/v), BSA 0.2% (w/v), SDS 2.0% (w/v) dissolved in 40 ml dH$_2$O, pH 7.4, add 2 ml 10 mg/ml sheared, denatured salmon sperm DNA, adjust volume to 50 ml with dH$_2$O. An equal volume of 20% dextran sulfate in formamide is added and the probe is denatured by boiling for 10 minutes. The prehybridization solution is removed from the hybridization bag and replaced with the denatured probe solution. This is incubated overnight at 42° C. with gentle agitation. The membranes then undergo two 5 min. washings at 65° C. with 2 ml/cm² 5X SSC (0.75 M NaCl, 0.075 M sodium citrate dihydrate) containing 0.5% SDS. Another washing at 50° C. for 30 min. in 2 ml/cm² of 0.1X SSC containing 1% (w/v) SDS follows, and a final 5 min. hybridization washing is performed with 2 ml/cm² of 2X SSC at room temperature. The binding of the streptavidin-DPIX conjugate, initiation of light production and film exposure is performed as described for the controls above. The resulting data demonstrates the production of chemiluminescence from DNA labeled with the nonmetallic tetrapyrrole molecule, DPIX.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for detecting in a sample the presence of the nonmetallic tetrapyrrole, deuteroporphyrin IX·2HCl having an oxidation potential, said method comprising:
   (a) contacting said sample with a signal solution which comprises, at a pH ranging from about 10 to 14, a luminescent reactant selected from the group consisting of luminol, isoluminol and a peroxyoxylate and at least one oxidant capable of overcoming the oxidation potential of said tetrapyrrole to produce, by means of chemiluminescence, emitted light;
   (b) measuring the light emitted in step (a); and
   (c) correlating said emitted light to the presence or absence of said tetrapyrrole in said sample.

2. The method of claim 1 wherein said oxidant is potassium superoxide.

3. The method of claim 1 wherein the chemiluminescent signal solution further comprises at least one electron transport facilitator, an anionic surfactant, glucose and a chelating agent.

4. The method of claim 1 wherein the signal solution comprises trans, trans-5-(4-Nitrophenyl)-2,4-pentadienal, sodium di-2-ethylhexyl sulfosuccinate, luminol or isoluminol, glucose, benzyltrimethylammonium hydroxide, cumene hydroperoxide, trisodium para periodate, potassium superoxide and EDTA.

5. A chemiluminescent system for emitting measurable light useful in a chemical assay, an immunoassay, a ligand binding assay or a nucleotide assay, said system comprising: at a pH ranging from about 10.0 to about 14.0, the nonmetallic tetrapyrrole, deuteroporphyrin IX·2HCl having an oxidation potential, a luminescent reactant selected from the group consisting of luminol, isoluminol and a peroxyoxylate and an oxidant or a combination of oxidants capable of overcoming the oxidation potential of the tetrapyrrole, said tetrapyrrole being bound to an analyte, or to a binding partner of an analyte or to a ligand of a bindig partner to an analyte.

6. The chemiluminescent system of claim 5 having only one oxidant wherein the oxidant is potassium superoxide.

7. The chemiluminescent system of claim 5 further comprising an electron transport facilitator, an ionic surfactant and a chelating agent.

8. The chemiluminescent system of claim 7 having a combination of oxidants wherein the electron transport facilitator is trans, trans-5-(4-Nitrophenyl)-2,4-pentadienal, the surfactant is sodium di-2-ethylhexyl sulfosuccinate, the luminescent reactant is luminol or isoluminol, the oxidants are benzyltrimethylammonium hydroxide, cumene hydroperoxide, trisodium para periodate and potassium superoxide, the chelating agent is EDTA, and the system further comprises glucose.

9. The chemiluminescent system of claim 5 wherein the analyte is a nucleic acid, an antigen, an antibody, a hapten, a hapten conjugate, a macromolecule, a protein or a polymer.

10. The chemiluminescent system of claim 5 wherein the binding partner is a nucleotide probe, an antigen, an antibody, a hapten, a hapten cojugate, a macromolecule, a protein or a polymer.

11. The chemiluminescent system of claim 5 wherein the ligand is an antigen, an antibody, a hapten, a hapten conjugate, a macromolecule, a protein or a polymer.

12. The chemiluminescent system of claim 5 wherein the nonmetallic tetrapyrrole is bound to the analyte, the binding partner of the analyte or to the ligand of a binding partner of the analyte by means of a biotin-avidin or biotin-streptavidin bridge.

13. A method for detecting the presence of or measuring the amount of an analyte in a sample comprising:
   (a) providing a solid phase coated with a specific binding partner for said analyte;
   (b) contacting said solid phase with said sample and with a predetermined amount of a deuteroporphyrin IX·2HCl-analyte conjugate, said deuteroporphyrin IX·2HCl having an oxidation potential, and with a predetermined amount of a polycation that prevents unbound deuteroporphyrin IX·2HCl-analyte conjugate from mediating luminescence, at least some of said specific binding partner binding to at least some of said deuteroporphyrin IX·2HCl-analyte conjugate;
   (c) contacting the solid phase from (b) with a signal solution comprising, at a pH ranging from about 10.0 to about 14.0, a luminescent reactant selected from the group consisting of luminol, isoluminol and a peroxyoxylate and an oxidant that overcomes or a combination of oxidants that overcome the oxidation potential of said deuteroporphyrin IX·2HCl in the bound deuteroporphyrin IX·2HCl-analyte conjugate to emit light; and
   (d) measuring the amount of light emitted in (c) wherein said amount of emitted light will be indirectly proportional to the amount of analyte present in said sample.

14. The method of claim 13 wherein the signal solution comprises luminol or isoluminol and potassium superoxide.

15. The method of claim 13 wherein said luminescent reactant is luminol or isoluminol, said oxidants are benzyltrimethylammonium hydroxide, cumene hydroperoxide, trisodium para periodate and potassium superoxide, and the signal solution further comprises trans, trans-5-(4-Nitrophenyl)-2,4-pentadienal, sodium di-2-ethylhexyl sulfosuccinate, EDTA and glucose.

16. A method for detecting the presence of or measuring the amount of an analyte in a sample comprising:

(a) providing a solid phase coated with a luminescent reactant selected from the group consisting of luminol, isoluminol and a peroxyoxylate and a specific binding partner for said analyte;

(b) contacting said solid phase with said sample and with a predetermined amount of deuteroporphyrin IX·2HCl-analyte conjugate, said deuteroporphyrin IX·2HCl having an oxidation potential, at least some of said binding partner binding to at least some of said deuteroporphyrin IX·2HCl-analyte conjugate;

(c) contacting the solid phase from (b) with a signal solution comprising, at a pH ranging from about 10.0 to about 14.0, an oxidant that overcomes or a combination of oxidants that overcome the oxidation potential of said deuteroporphyrin IX·2HCl in the bound deuteroporphyrin IX·2HCl-analyte conjugate to emit light; and (d) measuring the amount of light emitted in (c) wherein said amount of emitted light will be indirectly proportional to the amount of analyte present in said sample.

17. The method of claim 16 wherein the signal solution comprises potassium superoxide and the luminescent reactant is luminol or isoluminol.

18. The method of claim 16 wherein said luminescent reactant is luminol or isoluminol, said oxidants are benzyltrimethylammonium hydroxide, cumene hydroperoxide, trisodium para periodate and potassium superoxide, and the signal solution further comprises trans, trans-5-(4-Nitrophenyl)-2,4-pentadienal, sodium di-2-ethylhexyl sulfosuccinate, EDTA and glucose.

19. A method for detecting the presence of a first and second analyte in a sample comprising:

(a) providing a solid phase coated with a first specific binding partner and a second specific binding partner, said first binding partner being specific for said first analyte and said second binding partner being specific for said second analyte;

(b) contacting said solid phase with said sample and with a deuteroporphyrin IX·2HCL-first analyte conjugate and a luminescent label-second analyte conjugate, at least some of said first analyte conjugate binding to at least some of said first binding partner and at least some of said second analyte conjugate binding to at least some of said second binding partner;

(c) separating unbound conjugates from bound conjugates by washing the contacted solid phase;

(d) contacting the washed solid phase in (c) with either a signal solution specific for said luminescent label or a signal solution specific for said deuteroporphyrin IX·2HCL to produce light by means of a chemical reaction, said signal solution specific for said deuteroporphyrin IX·2HCL comprising, at a pH ranging from about 10.0 to about 14.0, a luminescent reactant selected from the group consisting of luminol, isoluminol and a peroxyoxylate, and an oxidant that overcomes, or a combination of oxidants that overcome the oxidation potential of said deuteroporphyrin IX·2HCL;

(e) detecting or measuring said light from said reaction in (d);

(f) contacting the solid phase from (d) with a signal solution specific for said luminescent label, if the signal solution in (d) was a solution specific for said deuteroporphyrin IX·2HCL, or with a signal solution specific for said deuteroporphyrin IX·2HCL, if the solution in (d) was a solution specific for said luminescent label, to produce light by means of a chemical reaction;

(g) detecting or measuring said light from said reaction in (f); and (h) detecting said first and said second analyte or determining the amount of said first or said second analyte from the light detected or measured in steps (e) and (g).

20. The method of claim 19 wherein the luminescent label is a luminescent acridinium derivative, lucigenin, a luminescent lucigenin derivative, luciferin or a luminescent luciferin derivative.

21. The method of claim 19 wherein the luminescent label is a luminescent acridinium derivative, lucigenin, a luminescent lucigenin derivative, luciferin or luminescent luciferin derivative and the signal solution specific for said nonmetallic tetrapyrrole further comprises potassium superoxide.

22. The method of claim 19 wherein the washed solid phase from (c) is contacted in step (f) with the signal solution specific for deuteroporphyrin IX·2HCl which comprises trans, trans-5-(4-Nitrophenyl)-2,4-pantadienal, sodium di-2-ethylhexyl sulfosuccinate, luminol or isoluminol, glucose, benzyltrimethylammonium hydroxide, cumene hydroperoxide, trisodium para periodate, and EDTA.

23. A method for detecting the presence of a first and second analyte in a sample comprising:

(a) providing a solid phase coated with a first specific binding partner and a second specific binding partner, said first binding partner being specific for said first analyte and said second binding partner being specific for said second analyte;

(b) contacting said solid phase with said sample and with a deuteroporphyrin IX·2HCl-first analyte conjugate and a luminescent label-second analyte conjugate, at least some of said first analyte conjugate binding to at least some of said first binding partner and a least some of said second analyte conjugate binding to at least some of said second binding partner;

(c) separating unbound conjugates from bound conjugates by washing the contacted solid phase;

(d) producing emitted light by contacting the washed solid phase in (c) with a chemiluminescent signal solution comprising, at a pH ranging from about 10.0 to about 14.0, a luminescent reactant selected from the group consisting of luminol, isoluminol and a peroxyoxylate and at least one oxidant capable of overcoming the oxidation potential of said deuteroporphyrin IX·2HCL, to produce emitted light resulting from chemiluminscence by means of both said deuteroporphyrin IX·2HCl and said luminescent label, said light emitted by means of said deuteroporphyrin IX·2HCl differing from said light emitted by means of said luminescent label;

(e) differentiating the light emitted in (d) and measuring said differentiated light to detect the presence of said first and second analyte.

24. A chemiluminescent system for producing measurable light be means of at least two different kinds of molecules and useful in a chemical assay, ligand binding assay, immunoassay or nucleotide assay for detecting more than one analyte in a sample comprising, at a pH ranging from about 10.0 to about 14.0, deuteroporphyrin IX·2HCl coupled to a first analyte or to a binding partner of said first analyte or to a ligand of a binding partner of said first analyte, a luminescent label coupled to a second analyte or to a binding partner of said second analyte or to a ligand of a binding partner of said second analyte, a luminescent reactant selected from the group consisting of luminol, isoluminol and peroxyoxylate, and the oxidant potassium superoxide or a combination of oxidants comprising benzyltrimethylammonium hydroxide, cumene hydroperoxide, trisodium para periodate and potassium superoxide.

25. The chemiluminescent systems of claim 24 further comprising an electron transport facilitator, an ionic surfactant and a chelating agent.

26. The luminescent system of claim 25 wherein the electron transport facilitator is trans,trans-5-(4-nitrophenyl)-2,4- pentadienal, the ionic surfactant is sodium di-2-ethylhexyl sulfosuccinate, the chelating agent is EDTA and further comprises glucose.

27. The luminescent system of claim 24 further comprising a predetermined amount of a polycation.

28. The luminescent system of claim 24 further comprising a predetermined amount of a polyanion.

29. The luminescent system of claim 29 wherein the analyte is a nucleic acid, an antigen, an antibody, a hapten, a hapten conjugate, a macromolecule, a protein or a polymer.

30. In a ligand binding assay method for determining the presence or measuring the concentration of an unknown amount of a bio-active analyte in a fluid sample wherein a labeled compound binds, directly or indirectly, to said analyte in an assay medium containing said sample, any unbound labeled compound is separated from bound labeled compound, and the presence or concentration of said analyte is detected by the presence or absence of a detectable or measurable reaction product generated by said label and a signal solution when the bound or unbound labeled compound is mixed with said signal solution. The improvement comprising using deuteroporphyrin IX·2HCl as the label and at a pH from about 10.0 to about 14.0, a mixture of trans,-trans-5-(4-nitrophenyl)-2,4-pentadienal, sodium di-2-ethylhexyl sulfosuccinate, luminol, glucose, benzyltrimethylammonium hydroxide, cumene hydroperoxide, trisodium para periodate, potassium superoxide and ethylenediaminetetraacetic acid as the signal solution.

31. In a method for detecting the presence or amount of an analyte in a sample that utilizes a signal solution and a luminescence mediating molecule-labeled compound wherein said luminescence mediating molecule labeled compound binds to said analyte or to a binding partner bound to said analyte or to a ligand of a binding partner bound to said analyte in an assay medium containing said sample, and the presence or concentration of said analyte is detected by the presence or absence of a detectable or measurable reaction product generated by said label and a signal solution when the bound or unbound labeled compound is mixed with said signal solution, the improvement comprises:

utilizing as said luminescence mediating moleculelabeled compound a deuteroporphyrin IX·2HCl-labeled compound, a predetermined amount of polycation that prevents said deuteroporphyrin IX·2HCl in unbound deuteroporphyrin IX·2HCl-labeled compounds from mediating luminescnece, and as said signal solution a solution comprising at a pH from about 10.0 to about 14.0, a luminescnet reactant selected from the group consisting of luminol, isoluminol and a peroxyoxylate and the oxidant potassium superoxide or the combination of oxidants benzyltrimethylammonium hydroxide, cumene hydroperoxide, trisodium para periodate and potassium superoxide.

32. In a ligand binding assay method for determining the presence or measuring the concentration of an unknown amount of a bio-active analyte in a fluid sample wherein a labeled competitive binding compound competes in an assay medium containing said sample with said analyte for binding directly or indirectly to an anti-analyte antibody specific for said analyte, any unbound labeled compound is separated from bound labeled compound, and the presence or concentration of said analyte is detected by the presence or absence of a detectable or measurable reaction product generated by said label and a signal solution when the bound or unbound labeled compound is mixed with said signal solution. The improvement comprising using deuteroporphyrin IX·2HCl as the label and at a pH from about 10.0 to about 14.0, a mixture of trans,trans-5-(4-nitrophenyl)-2,4-pentadienal, sodium di-2-ethylhexyl sulfosuccinate, luminol, glucose, benzyltrimethylammonium hydroxide, cumene hydroperoxide, trisodium para periodate, potassium superoxide and ethylenediaminetetraacetic acid as the signal solution.

* * * * *

UNITED STATES PATENT AND TRADEMARK OFFICE
CERTIFICATE OF CORRECTION

PATENT NO. : 5,340,714
DATED : August 23, 1994
INVENTOR(S) : George W. Katsilometes Page 1 of 3

It is certified that error appears in the above-indentified patent and that said Letters Patent is hereby corrected as shown below:

Column 3, line 7, please change "177'201" to read --177-201--;

line 41, please change "pi, pi," to read --pi, pi".

Column 8, line 54, please change ""AE"0" to read --"AE"--.

Column 9, line 5, please delete the --.-- after "acridinium".

Column 11, line 14, please change "10⁻⁻" to read --$10^{-18}$--.

Column 12, line 2, please change "trnas-trans" to read --trans-trans--.

Column 16, line 16, please change "0.004-0,025" to read --0.004-0.025--;

lines 28 and 35, please change "vitamin $B_2$" to read --vitamin $B_{12}$--.

Column 17, line 32, please add --.-- after "luminometer".

Column 19, line 62, please add --.-- after "(see FIG. 9c and 9d)".

UNITED STATES PATENT AND TRADEMARK OFFICE
CERTIFICATE OF CORRECTION

PATENT NO. : 5,340,714
DATED : August 23, 1994
INVENTOR(S) : George W. Katsilometes It is certified that error appears in the above-indentified patent and that said Letters Patent is hereby corrected as shown below:

Column 20, line 33, please change "0,083" to read --0.083--;

line 34, please change "12,465" to read --12.465--;

line 43, please change "(NAN3)" to read --(NaN$_3$)--.

Column 21, approximately line 32, please change "1762" to read --17$\beta$--;

approximately line 50, please insert --.-- after "range".

Column 22, line 20, please change ".2.7:383" to read --27:383--.

Column 24, line 7, please delete the "-" after "DPIX+".

Column 25, line 43, please change "12.5X" to read --2.5X--.

IN THE CLAIMS:

Column 27, line 65, please change "bindig" to read --binding--.

Column 32, line 16, please change "luminescnece" to read --luminescence--;

UNITED STATES PATENT AND TRADEMARK OFFICE
CERTIFICATE OF CORRECTION

PATENT NO. : 5,340,714

DATED : August 23, 1994

INVENTOR(S) : George W. Katsilometes

It is certified that error appears in the above-indentified patent and that said Letters Patent is hereby corrected as shown below:

Column 27, line 18, please change "luminescnet" to read --luminescent--.

Signed and Sealed this

Third Day of January, 1995

Attest:

BRUCE LEHMAN

*Attesting Officer*  *Commissioner of Patents and Trademarks*